(12) United States Patent
Woo et al.

(10) Patent No.: US 11,172,840 B2
(45) Date of Patent: Nov. 16, 2021

(54) DEVICE FOR SUBJECT IMAGE MONITORING, METHOD THEREFOR, AND SYSTEM FOR IMAGE MONITORING

(71) Applicant: Bilab Co., Ltd., Seoul (KR)

(72) Inventors: Eung Je Woo, Bundang-gu (KR); Tong In Oh, Hwaseong-si (KR)

(73) Assignee: BILAB CO., LTD.

( * ) Notice: Subject to any disclaimer, the term of this patent is extended or adjusted under 35 U.S.C. 154(b) by 0 days.

(21) Appl. No.: 16/462,142

(22) PCT Filed: Nov. 15, 2017

(86) PCT No.: PCT/KR2017/012923
§ 371 (c)(1),
(2) Date: May 17, 2019

(87) PCT Pub. No.: WO2018/093136
PCT Pub. Date: May 24, 2018

(65) Prior Publication Data
US 2019/0328268 A1    Oct. 31, 2019

(30) Foreign Application Priority Data

Nov. 18, 2016 (KR) .......................... 10-2016-0154145

(51) Int. Cl.
*G06K 9/00* (2006.01)
*A61B 5/0536* (2021.01)
*A61B 5/0295* (2006.01)
*A61B 5/085* (2006.01)
*G06T 7/00* (2017.01)

(52) U.S. Cl.
CPC .......... *A61B 5/0536* (2013.01); *A61B 5/0295* (2013.01); *A61B 5/085* (2013.01); *G06T 7/0012* (2013.01); *G06T 2207/30061* (2013.01)

(58) Field of Classification Search
CPC ..... A61B 5/0536; A61B 5/0295; A61B 5/085; G06T 7/0012; G06T 2207/30061
See application file for complete search history.

(56) References Cited

U.S. PATENT DOCUMENTS

2003/0216664 A1* 11/2003 Suarez ................. A61B 5/0536
600/547

* cited by examiner

*Primary Examiner* — Atiba O Fitzpatrick
(74) *Attorney, Agent, or Firm* — Renaissance IP Law Group LLP

(57) ABSTRACT

Disclosed are an image monitoring apparatus and method for displaying a lung ventilation impedance image and a lung perfusion impedance image based on impedance data measured at a thorax of a subject, and a reference image based on a biometric signal, in which impedance data based on voltage measured at the thorax of the subject is separated into lung ventilation impedance data and lung perfusion impedance data, and dynamic bloodstream change data in a heart and blood vessels by electrical impedance tomography (EIT); and a lung ventilation impedance image, a lung perfusion impedance image, and a heart and blood vessel impedance image, which are obtained by the separation, and a reference image based on a biometric signal sensed at a part of the subject targeted to be examined are displayed according to a pathological condition of the subject.

13 Claims, 21 Drawing Sheets

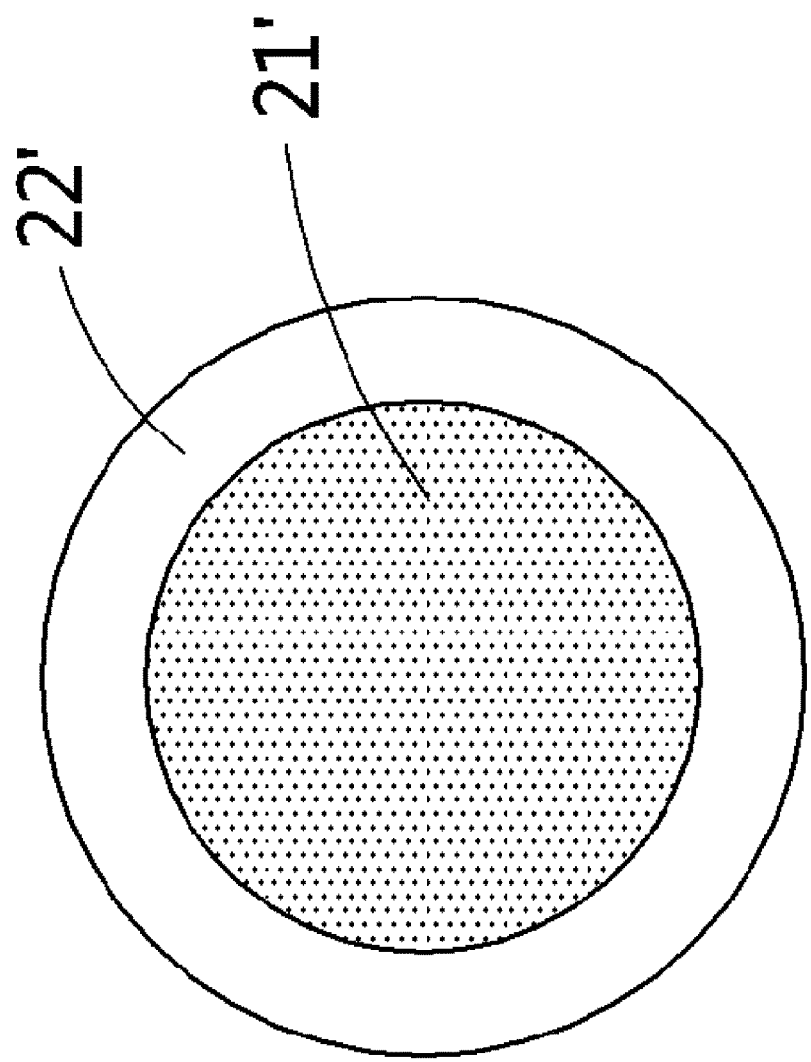

DEVICE FOR SUBJECT IMAGE MONITORING, METHOD THEREFOR, AND SYSTEM FOR IMAGE MONITORING

TECHNICAL FIELD

The disclosure relates to an image monitoring method, apparatus and system for providing biometric state information about a subject as a moving image in real time anywhere, and an image monitoring system, and more particularly to an image monitoring method, apparatus and system for simultaneously measuring and analyzing a lung ventilation impedance image, a lung perfusion impedance image and a bloodstream impedance image corresponding to electrical property change measured at a thorax of a subject and a biometric signal related to dynamic change in bloodstream and respiration sensed at parts of the subject targeted to be examined, and providing physiological and pathological state information about the subject in the form of a real-time moving image and a signal.

BACKGROUND ART

A patient monitoring device (or a patient monitor) obtains biometric state information of a subject through a plurality of sensors by an invasive or noninvasive method, outputs a plurality of biometric signals and digitized information extracted from the obtained biometric state information to a screen in real time, and gives an alarm in the form of a wired, wireless or warning sound when the output signal or value is beyond a set range.

A conventional patient monitoring device receives and processes a biometric signal measured from a sensor (or an electrode) attached to a body skin of a subject and a sensor inserted in a human body, and outputs a numerical value, a figure, a value and a waveform varied depending on time. Such a conventional patient monitoring device receives and displays at least one biometric signal (or bio signal) among electrocardiogram (ECG), saturation of peripheral oxygen, ($SpO_2$), end-tidal carbon dioxide ($EtCo_2$), blood pressure (BP), respiration, and temperature and thus functions to monitor general change in a body condition, such as respiration of a subject, dynamic change in bloodstream, etc. in real time, but has a limit on obtaining local change of an inner body of biometric information that can be measurable by only an invasive method.

Further, a lung ventilation impedance image and a lung perfusion impedance image of a subject, which can be obtained by an electrical impedance tomography (EIT) method have a limit on analyzing a body condition of a subject from change in impedance varied depending on various causes.

In other words, the conventional patient monitoring device employs a method of outputting only a biometric time-varying signal (bio-signal) of a subject, and therefore does not provide an image in a certain area in a lung and heart of a subject, a lung ventilation impedance image, a lung perfusion impedance image, and information about blood flow in the heart and a major blood vessel, or needs an invasive method to measure these information, thereby having a problem with monitoring physiological and pathological states of a subject more accurately in real time.

DISCLOSURE

Technical Problem

The disclosure is to provide an image monitoring apparatus, method and system for a subject, in which lung ventilation impedance data, lung perfusion impedance data, and bloodstream impedance data about blood flow in a heart and major blood vessels, which are separated from impedance data based on voltage measured at a thorax of the subject, are received from an electrical impedance tomography (EIT) device using an EIT method and displayed as a moving image and a numerical value.

Further, the disclosure is to provide an image monitoring apparatus, method and system for a subject, in which a lung ventilation impedance image, a lung perfusion impedance image, and a cardiopulmonary dynamic bloodstream impedance image respectively based on lung ventilation impedance data, lung perfusion impedance data, and bloodstream impedance data about blood flow in a heart and major blood vessels, and reference time-varying data of a biometric signal sensed at parts of the subject targeted to be examined are collectively analyzed to display indexes showing physiological and pathological states of the subject.

Further, the disclosure is to provide an image monitoring apparatus, method and system for a subject, in which a biometric signal measured in real time from a body of a subject is used to suppress interference caused by different biometric signals of impedance data based on voltage measured at a thorax, and a signal separating algorithm for separating only signal components about local change is used in terms of an algorithm to separate lung ventilation impedance data, lung perfusion impedance data, and bloodstream impedance data about blood flow in the heart and major blood vessels, thereby providing local biometric state information and an impedance image for monitoring a cardiopulmonary function more accurately in real time.

Technical Solution

According to an embodiment of the disclosure, an image monitoring apparatus includes: a data receiver configured to receive lung ventilation impedance data, lung perfusion impedance data and bloodstream impedance data of a heart and blood vessels, which are based on voltage measured at a thorax of a subject and separated by an electrical impedance tomography (EIT) device, and a biometric signal, which is sensed at a part of the subject targeted to be examined; an image processor configured to generate a lung ventilation impedance image, a lung perfusion impedance image and a bloodstream impedance image based on the lung ventilation impedance data, the lung perfusion impedance data and the bloodstream impedance data, and a reference image based on the sensed biometric signal; and a controller configured to control at least one of the lung ventilation impedance image, the lung perfusion impedance image, the bloodstream impedance image and the reference image to be displayed according to screen modes and measurement parts.

According to an embodiment of the disclosure, an image monitoring system includes: an EIT device configured to selectively supply electric currents to at least one pair of electrodes selected among a plurality of electrodes attached along a chest circumference of a subject, separate lung ventilation impedance data, lung perfusion impedance data and bloodstream impedance data of a heart and blood vessels, which are based on impedance data obtained by measuring voltage through unselected electrodes, and sense a biometric signal at a part of the subject targeted to be examined; and an image monitoring apparatus configured to at least one of a lung perfusion impedance image, a bloodstream impedance image based on the lung ventilation impedance data, the lung perfusion impedance data and the bloodstream impedance data, and a reference image based on the sensed biometric signal.

According to an embodiment of the disclosure, an image monitoring method of monitoring a state of a subject in real time through an image monitoring apparatus includes: receiving lung ventilation impedance data, lung perfusion impedance data and bloodstream impedance data of a heart and blood vessels, which are based on voltage measured at a thorax of a subject and separated by an electrical impedance tomography (EIT) device, and receiving a biometric signal, which is sensed at a part of the subject targeted to be examined; generating a lung ventilation impedance image, a lung perfusion impedance image and a bloodstream impedance image based on the lung ventilation impedance data, the lung perfusion impedance data and the bloodstream impedance data, and generating a reference image based on the sensed biometric signal; and controlling at least one of the lung ventilation impedance image, the lung perfusion impedance image, the bloodstream impedance image and the reference image to be displayed according to screen modes and measurement parts.

Advantageous Effects

According to an embodiment of the disclosure, lung ventilation impedance data, lung perfusion impedance data, and bloodstream impedance data about blood flow in a heart and major blood vessels, which are separated from impedance data based on voltage measured at a thorax of the subject, are received from an electrical impedance tomography (EIT) device using an EIT method and displayed as a moving image and a numerical value.

Further, according to an embodiment of the disclosure, a lung ventilation impedance image, a lung perfusion impedance image, and a cardiopulmonary dynamic bloodstream impedance image respectively based on lung ventilation impedance data, lung perfusion impedance data, and bloodstream impedance data about blood flow in a heart and major blood vessels, and reference time-varying data of a biometric signal sensed at parts of the subject targeted to be examined are collectively analyzed to display indexes showing physiological and pathological states of the subject.

Further, according to an embodiment of the disclosure, a biometric signal measured in real time from a body of a subject is used to suppress interference caused by different biometric signals of impedance data based on voltage measured at a thorax, and a signal separating algorithm for separating only signal components about local change is used in terms of an algorithm to separate lung ventilation impedance data, lung perfusion impedance data, and bloodstream impedance data about blood flow in the heart and major blood vessels, thereby providing local biometric state information and an impedance image for monitoring a cardiopulmonary function more accurately in real time.

DESCRIPTION OF DRAWINGS

FIGS. 9A and 9B schematically illustrate a complex electrode employed in the EIT device shown in FIG. 8B.

DETAILED DESCRIPTION OF THE INVENTION

Below, embodiments of the disclosure will be described with reference to accompanying drawings and content shown the accompanying drawings without limiting the disclosure to the embodiments.

The terminology used herein is for the purpose of describing embodiments only and is not intended to be limiting of the disclosure. As used herein, the singular forms are intended to include the plural forms as well, unless the context clearly indicates otherwise. It will be further understood that the terms "comprises" and/or "comprising" when used herein specify the presence of stated elements, steps, operations, and/or components, but do not preclude the presence or addition of one or more other elements, steps, operations, and/or components.

A certain aspect or design disclosed in "embodiment," "example," "facet," "illustration," etc. used herein should not be construed to be better or more advantageous than other aspects or designs.

Further, terms 'or' are intended to indicate 'inclusive or' rather than 'exclusive or'. In other words, unless mentioned otherwise or the context clearly indicates otherwise, 'x employs a or b' is intended to mean any of the natural inclusive permutations.

Further, articles "a" or "an" as used in the present specification and claims should generally be construed to mean "one or more" unless specified otherwise or clear from context to be directed to a singular form.

Further, it will be understood that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined here.

Meanwhile, in the following description, well-known functions or configurations will not be described in detail because they may obscure the gist of the disclosure. Further, the terminologies to be described below are defined in consideration of the functions within the scope of the disclosure and may vary depending on a user's or operator's intention or practice. Accordingly, some definitions are implied based on the content throughout the specification.

Figure 1:
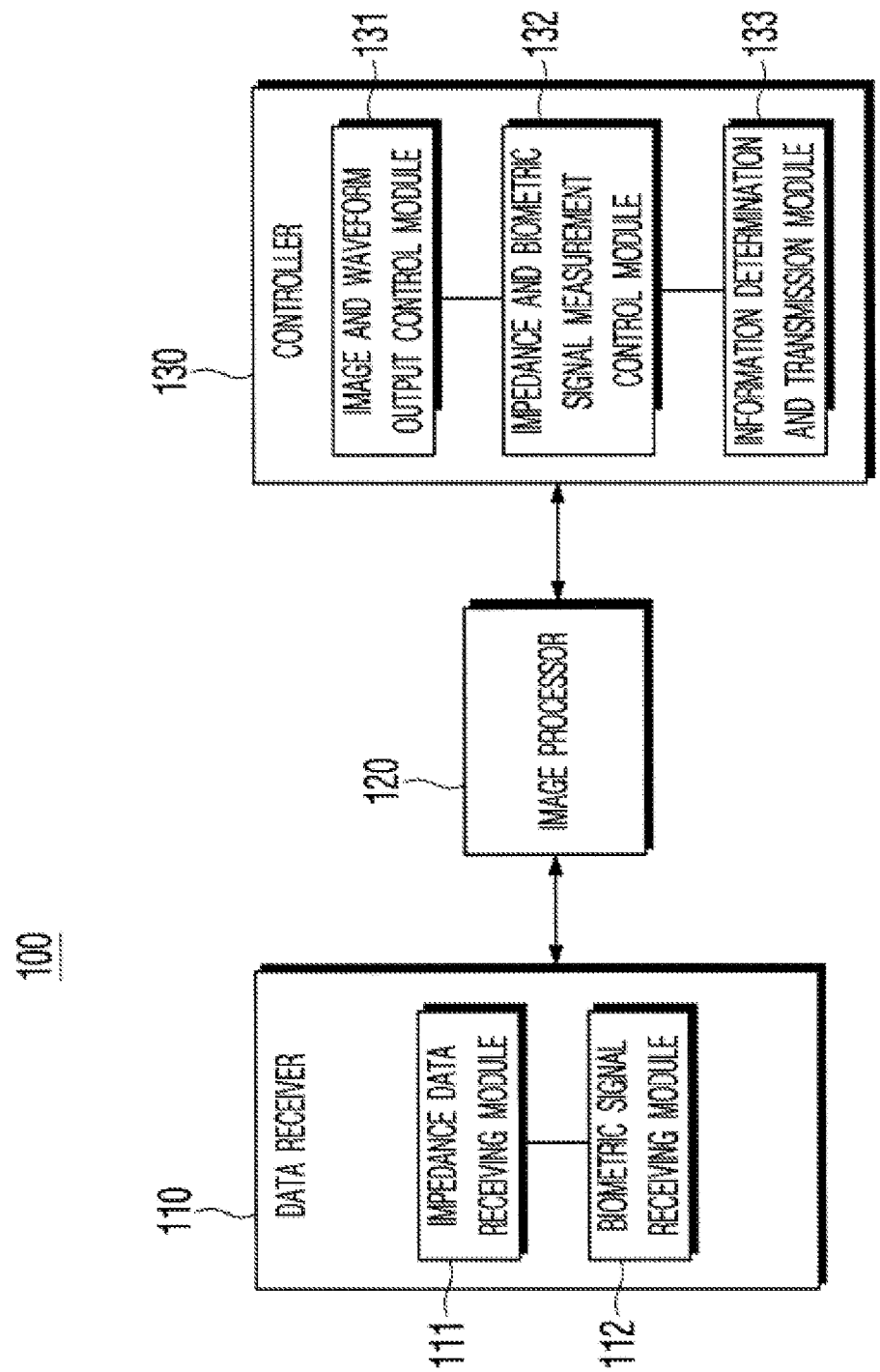
FIG. 1 is a block diagram of an image monitoring apparatus according to an embodiment of the disclosure.

FIG. 1 is a block diagram of an image monitoring apparatus according to an embodiment of the disclosure.

Referring to FIG. 1, an image monitoring apparatus 100 according to an embodiment of the disclosure receives separated lung ventilation impedance data, lung perfusion impedance data, and bloodstream impedance data and a biometric signal from an electrical impedance tomography (EIT) device, and thus displays a lung ventilation impedance image, a lung perfusion impedance image, a bloodstream impedance image and a reference image as indexes for showing physiological and pathological states of a subject.

To this end, the image monitoring apparatus 100 according to an embodiment of the disclosure includes a data receiver 110, an image processor 120, and a controller 130.

The data receiver 110 receives separated lung ventilation, lung perfusion and bloodstream impedance data varied depending on blood flow in a heart and major blood vessels, which are based on voltage measured at a thorax of a subject, from the EIT device, and a biometric signal sensed at parts of the subject targeted to be examined.

In more detail, the data receiver 110 includes an impedance data receiving module 111 and biometric signal receiving module 112.

The impedance data receiving module 111 may receive at least one pieces of separated impedance data among the lung ventilation impedance, the lung perfusion impedance and the bloodstream impedance, which are based on the voltage measured at the thorax of the subject, from the EIT device.

For example, the lung ventilation impedance data and the lung perfusion impedance data may be obtained based on the voltage measured through unselected electrodes by supplying electric currents to at least one pair of electrodes selected among a plurality of electrodes attached along a chest circumference of a subject.

The lung ventilation impedance data is obtained based on a lung ventilation (or pulmonary ventilation) process of a subject, and the lung ventilation process may refer to a process of moving air in and out while the subject continuously and periodically breathes in and out.

The lung perfusion impedance data refers to data showing blood in a lung of a subject, by which it is possible to check how equally the blood is distributed in both lungs of the subject. Thus, it is possible to observe and diagnose pulmonary vascular diseases such as pulmonary embolism, thrombus, tumor, lung cancer, tuberculosis and granuloma; occlusive diseases such as chronic bronchitis, pulmonary emphysema, bronchial asthma and bronchiectasis; and other diseases such as pneumonia, pulmonary infarction, pleural effusion and pneumothorax.

The bloodstream impedance data refers to data showing a degree of change in blood flow in a heart and major blood vessels of a subject, by which it is possible to check a heart rate, a blood flow rate and corresponding oxygen breathing capacity, and change in blood flow in major blood vessels in a thorax.

Further, the biometric signal receiving module 112 may be configured to receive a biometric signal sensed at parts of the subject targeted to be examined from the EIT device.

The biometric signal refers to data obtained by sensing at parts (i.e. body parts) of the subject targeted to be examined, which may be sensed by a plurality of sensors.

According to an embodiment, the biometric signal may be a sensing signal from at least one sensor among a sound sensor, a posture sensor and an electrocardiogram (ECG) sensor, and may include at least one among a saturation of peripheral oxygen ($SpO_2$) signal, a photoplethysmography (PPG) signal, and an ECG signal.

According to an alternative embodiment, the biometric signal may be a signal obtained by sensing electroencephalogram (EEG), electromyogram (EMG), electrooculogram (EOG), seismocardiography (SCG) and ballistocardiography (BCG) of a thorax of a subject.

The EIT device may be configured to obtain the impedance data by measuring voltage at a thorax of a subject, and the EIT device may sense a biometric signal at parts of the subject targeted to be examined. Further, the lung ventilation impedance data and the lung perfusion impedance data may be extracted from the obtained impedance data based on a simultaneously measured biometric signal.

To this end, the EIT device may include a thorax electrode element (not shown), a sensing element (not shown), an impedance data obtainer (not shown), an algorithm function element (not shown), and an EIT controller (not shown).

The thorax electrode element may be provided with a plurality of electrodes for current injection and voltage detection, and attached along a chest circumference of a subject to be examined.

The sensing element may be in contact with parts of the subject targeted to be examined and sense the biometric signal.

The impedance data obtainer may obtain the impedance data with regard to the thorax of the subject based on the voltage measured from the plurality of electrodes.

The algorithm function element may separate the lung ventilation impedance data, the lung perfusion impedance data, and the bloodstream impedance data related to blood flow in a heart and major blood vessels by applying the signal separating algorithm and the simultaneously measured biometric signal to the obtained impedance data.

For example, the algorithm function element applies an independent component analyses (ICA) algorithm, i.e. a signal separating algorithm to the obtained impedance data to separate the lung ventilation impedance data, the lung perfusion impedance data and the bloodstream impedance data, which are different from one another, and applies a signal magnitude restoration algorithm to each piece of the separated impedance data to be restored to have a magnitude of an original signal.

The EIT controller may perform control to selectively supply electric currents to at least one pair of electrodes selected among the plurality of electrodes, measure voltage through unselected electrodes, and transmit the sensed biometric signal, the lung ventilation impedance data, the lung perfusion impedance data and the bloodstream impedance data.

Specific configurations and features of the EIT device will be described in detail with reference to FIGS. 6 to 11B.

The image processor 120 generates the lung ventilation impedance image, the lung perfusion impedance image and the bloodstream impedance image based on the lung ventilation impedance data, the lung perfusion impedance data and the bloodstream impedance data, and generates the reference image based on the sensed biometric signal.

In more detail, the image processor 120 may restore the lung ventilation impedance image and the lung perfusion impedance image of conductivity and permittivity images about the interior of the thorax of the subject and the bloodstream impedance data related to blood flow in a heart and major blood vessels from the lung ventilation impedance data, the lung perfusion impedance data and the bloodstream impedance data, respectively.

Thus, the image processor 120 may calculate at least one of average deviation, average variation, average phase delay, and an average absolute impedance value according to change in data based on the lung ventilation impedance image, the lung perfusion impedance image and the bloodstream impedance image.

Further, the image processor 120 may quantify at least one of change, degree and pattern of ventilation inside a lung over time based on the lung ventilation impedance image, and may quantify at least one of change, degree and pattern of perfusion inside the lung over time based on the lung perfusion impedance image.

Further, the image processor 120 may quantify at least one of dynamic bloodstream change, degree and pattern in a heart and blood vessels over time based on the bloodstream impedance images of the heart and major blood vessels by applying the sensed biometric signal.

Further, the image processor 120 may be configured to generate a reference image having a waveform and a numerical value over time based on the sensed biometric signal, and calculate at least one among the average deviation, the average variation and the average phase delay of the biometric signal.

According to an embodiment, the image processor 120 may be configured to collectively analyze the physiological and pathological states of the subject based on the lung ventilation impedance data, the lung perfusion impedance data, the bloodstream impedance data, and the biometric signal.

The controller 130 may be configured to control at least one of the lung ventilation impedance image, the lung perfusion impedance image, the bloodstream impedance image and the reference image to be displayed according to screen modes and measurement parts.

In more detail, the controller 130 may include an image and waveform output control module 131, an impedance and biometric signal measurement control module 132, and an information determination and transmission module 133.

The image and waveform output control module 131 may be configured to control at least one of the calculated average values, the quantified lung ventilation impedance image, the quantified lung perfusion impedance image and the quantified bloodstream impedance image to be displayed according to preset screen modes or measurement parts of the subject desired to be monitored.

The measurement part may refer to a part to be more accurately monitored with regard to a state of at least one among a lung, a heart and major vessels of a subject.

In more detail, the image and waveform output control module 131 may be configured to control an image, a waveform, and a numerical value to be displayed in connection with at least one measurement data among the average deviation, the average variation, the average phase delay and the average absolute impedance value according to change in the calculated impedance data based on the lung ventilation impedance image, the lung perfusion impedance image and the bloodstream impedance image quantified by the image processor 120.

Further, the image and waveform output control module 131 may be configured to control the lung ventilation impedance image, the lung perfusion impedance image, the bloodstream impedance image and the measurement data to be displayed as an image, a waveform, and a numerical value based on screen modes and measurement parts set according to the preset physiological and pathological states of the subject.

Further, the image and waveform output control module 131 may be configured to control the reference image of the biometric signal, sensed at a part of the subject targeted to be examined, to be displayed as an image, a waveform, and a numerical value based on a preset screen mode.

Here, the screen mode may include a plurality of screen areas divided based on a certain pathological state of a subject to display the lung ventilation impedance image, the lung perfusion impedance image, and the reference images of the measurement data and biometric signal.

According to an embodiment, the controller 130 may control the lung ventilation impedance image, the lung perfusion impedance image, the bloodstream impedance image and the reference image to be arranged and displayed based a certain pathological state of a subject according to one of pulmonary vascular diseases (e.g. pulmonary embolism, thrombus, tumor, lung cancer, tuberculosis and granuloma), occlusive diseases (e.g. chronic bronchitis, pulmonary emphysema, bronchial asthma and bronchiectasis), and other diseases (e.g. pneumonia, pulmonary infarction, pleural effusion and pneumothorax).

The lung ventilation impedance image, the lung perfusion impedance image, the bloodstream impedance image, the reference image and the measurement data may be required differently according to a certain pathological state, and thus properly arranged and displayed by taking the pathological state into account.

According to an alternative embodiment, the image and waveform output control module 131 may be configured to control the lung ventilation impedance image, the lung perfusion impedance image, the bloodstream impedance image and the reference images corresponding to the measurement data and the biometric signal to be displayed with different colors, sizes, thicknesses, languages, sounds and voices, and control at least one warning signal to be given in the form of sound, vibration and color variance in a case of being out of a preset normal range.

The impedance and biometric signal measurement control module 132 may be configured to control the EIT device to measure the lung ventilation impedance data, the lung perfusion impedance data and the biometric signal at the thorax of the subject, and transmit a control signal for controlling measurement of the bloodstream impedance data about blood flow in a heart and major blood vessels to which the measured biometric signal is applied.

The information determination and transmission module 133 may be configured to control features to be performed by the data receiver 110 and the image processor 120, and transmit the received lung ventilation impedance data, lung perfusion impedance data, bloodstream impedance data, and biometric signal to the image processor 120 so that the lung ventilation impedance data, lung perfusion impedance data, bloodstream impedance data, and biometric signal can be generated as images.

Further, the information determination and transmission module 133 may be configured to control at least one of the received lung ventilation impedance data, lung perfusion impedance data, bloodstream impedance data, and biometric signal and the generated lung ventilation impedance image, lung perfusion impedance image, bloodstream impedance image and reference image to be transmitted to the outside.

Figure 2:
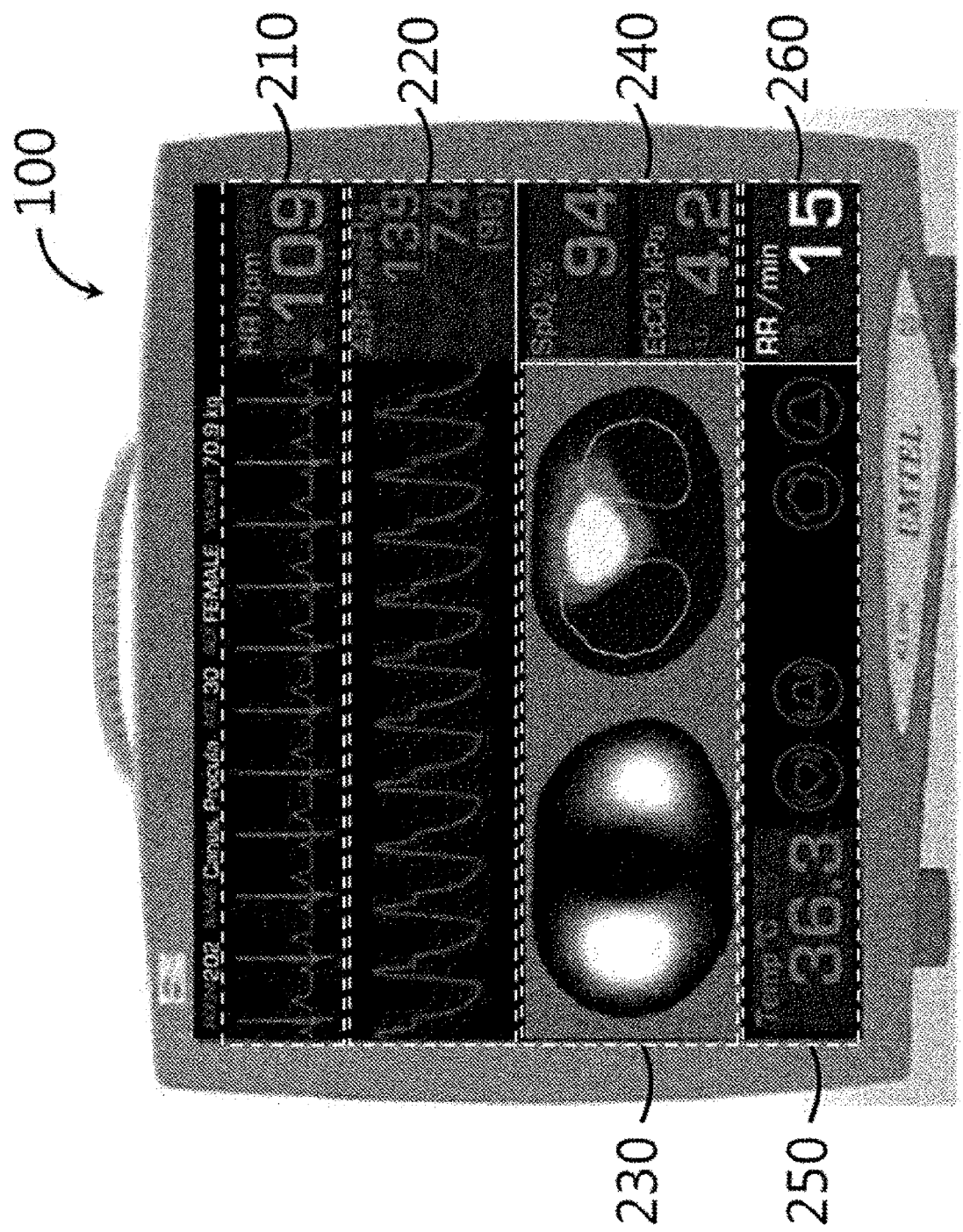
FIG. 2 illustrates an example of a display of an image monitoring apparatus according to an embodiment of the disclosure.

FIG. 2 illustrates an example of a display of an image monitoring apparatus according to an embodiment of the disclosure.

Referring to FIG. 2, the image monitoring apparatus 100 according to an embodiment of the disclosure displays an image, a waveform, and a numerical value based on pulse data (HR) 210, blood pressure data (ABP) 220, lung ventilation impedance image and lung perfusion impedance image 230, saturation of peripheral oxygen and end-expiration carbon dioxide partial pressure data (SpO2/EtCo2) 240, temperature data (Temp) 250 and respiration rate data (RR) 260.

The pulse data 210, the blood pressure data 220, the saturation of peripheral oxygen and end-expiration carbon dioxide partial pressure data 240, the temperature data 250, and the respiration rate data 260 may be displayed with different numerical values, waveforms and colors based on the signals sensed at parts of the subject targeted to be examined.

The lung ventilation impedance image and the lung perfusion impedance image 230 are restored from the lung ventilation impedance data and the lung perfusion impedance data received from the EIT device.

Thus, the image monitoring apparatus 100 according to an embodiment of the disclosure may display certain areas detected corresponding to lung ventilation and lung perfusion with red or blue color on the lung ventilation impedance image and the lung perfusion impedance image 230 generated based on the interior of the thorax of the subject.

The image monitoring apparatus 100 according to an embodiment of the disclosure may display more various pieces of data based on a pathological state of a subject in addition to the data shown in FIG. 2, and there are no limits to their display positions, numbers and sizes.

Further, the image monitoring apparatus 100 according to an embodiment of the disclosure may display the pulse data 210, the blood pressure data 220, the lung ventilation impedance image and the lung perfusion impedance image 230, the saturation of peripheral oxygen and end-expiration carbon dioxide partial pressure data 240, the temperature data 250 and the respiration rate data 260, which are varied in real time depending on the lung ventilation impedance data, the lung perfusion impedance data and the biometric signal of the subject measured in real time. Besides, the BCG, the SCG, and the like biometric signals about dynamic bloodstream change in a heart may be additionally displayed together.

Therefore, the image monitoring apparatus 100 according to an embodiment of the disclosure may display local respiration of a subject and corresponding cardiomotility, and bloodstream circulation as moving images.

Figure 3A:
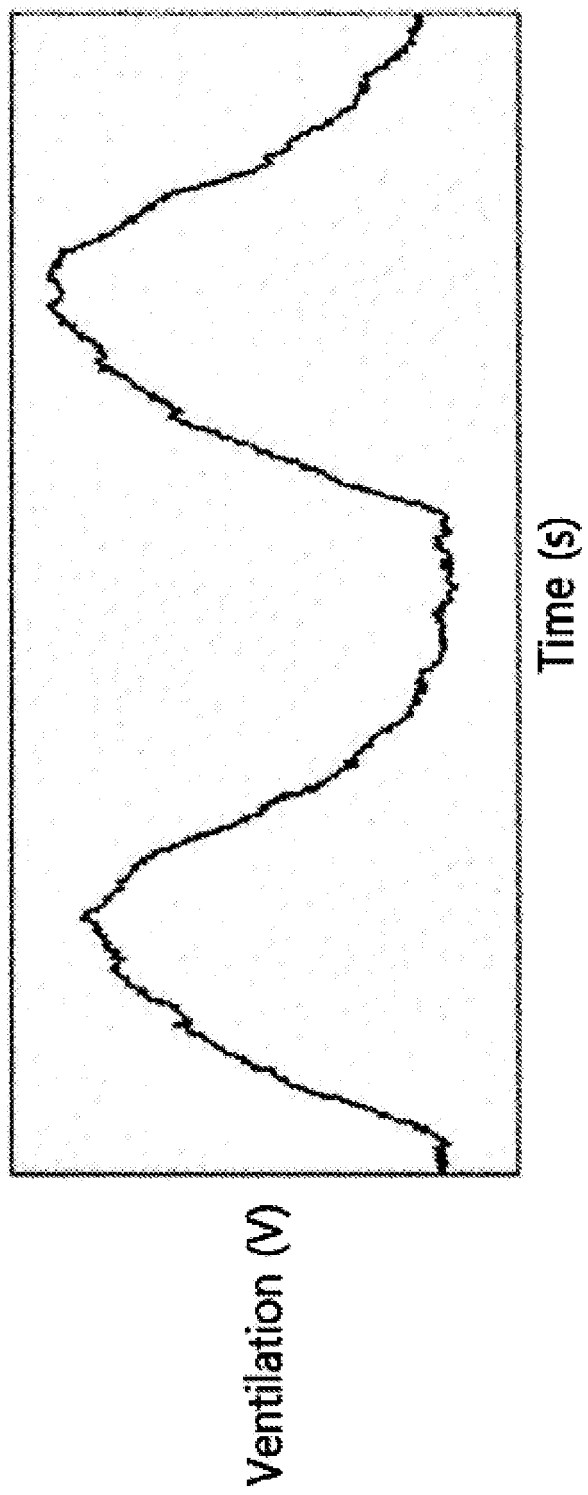
FIGS. 3A and 3B illustrate examples of lung ventilation impedance data and a lung ventilation impedance image.
Figure 3B:
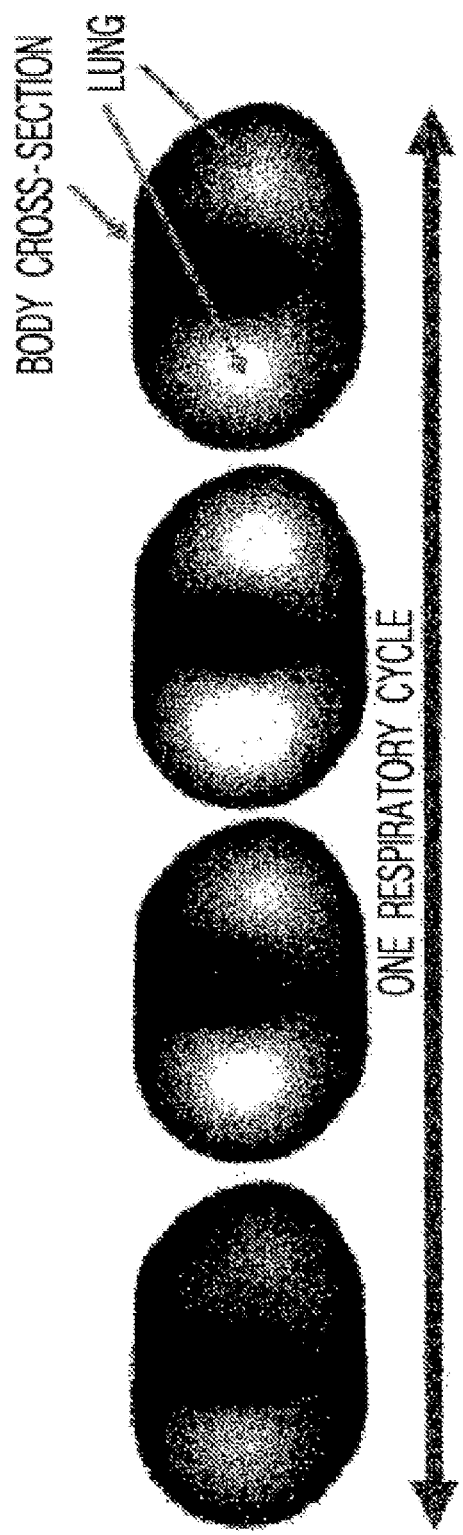

FIGS. 3A and 3B illustrate examples of lung ventilation impedance data and a lung ventilation impedance image.

The image monitoring apparatus according to an embodiment of the disclosure may be configured to obtain lung ventilation impedance data over time from the EIT device as shown in FIG. 3A, and monitors a lung ventilation impedance image based on the lung ventilation impedance data measured by electrodes attached to a chest circumference as shown in FIG. 3B.

That is, referring to FIG. 3B, the lung ventilation impedance image shows distribution of air inhaled to and exhaled from a lung by respiratory movement (one respiratory cycle) of a subject.

Figure 4A:
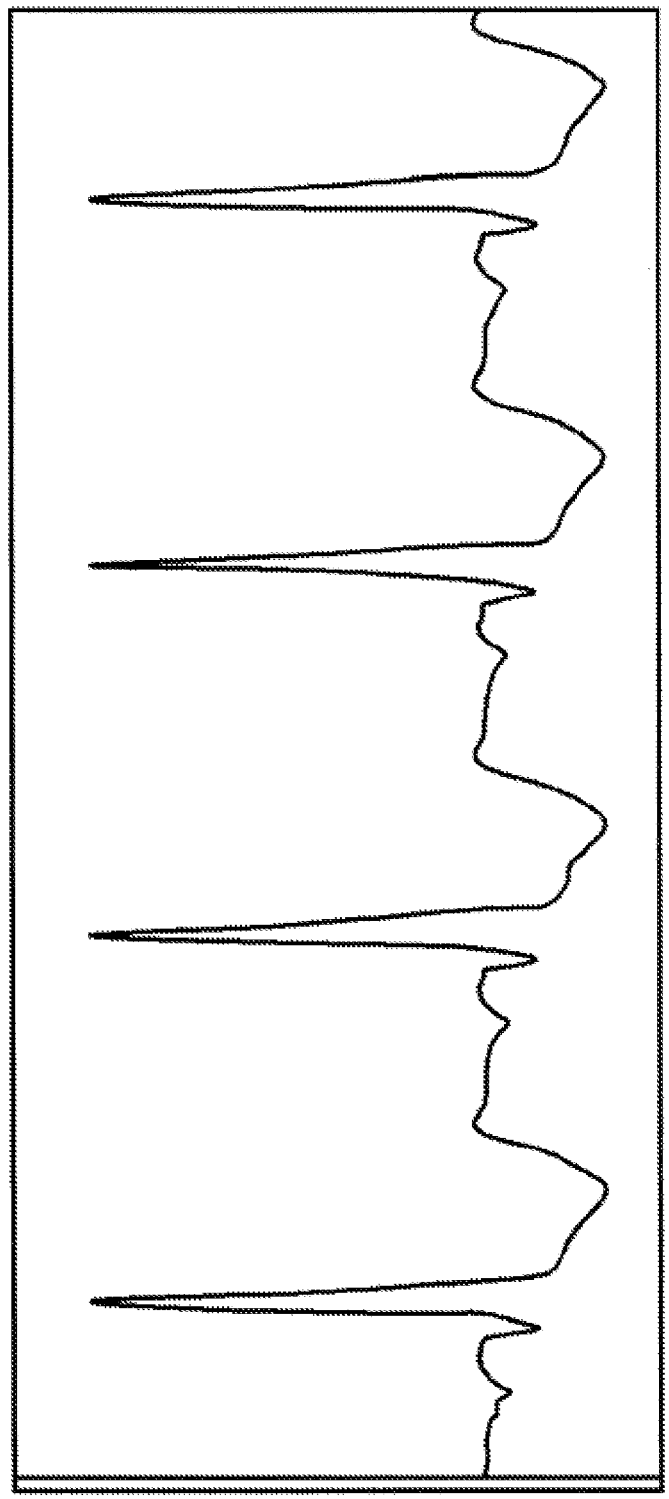
FIGS. 4A and 4B illustrate examples of electrocardiogram (ECG) and an impedance image based on blood flow inside the heart and lung.
Figure 4B:
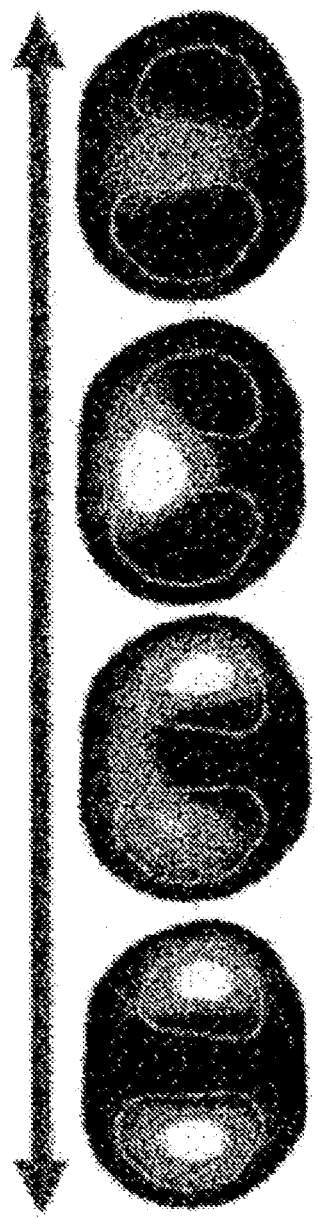

FIGS. 4A and 4B illustrate examples of ECG and an impedance image based on blood flow inside a heart and lung.

The image monitoring apparatus according to an embodiment of the disclosure may be configured to obtain lung perfusion impedance data synchronized with the ECG over time from the EIT device as shown in FIG. 4A, and monitor a lung perfusion impedance image based on the lung perfusion impedance data measured by electrodes attached along a chest circumference as shown in FIG. 4B.

That is, as shown in FIG. 4B, the lung perfusion impedance image may show distribution of blood in both lungs of a subject and blood flow in a heart and major blood vessels.

Figure 5:
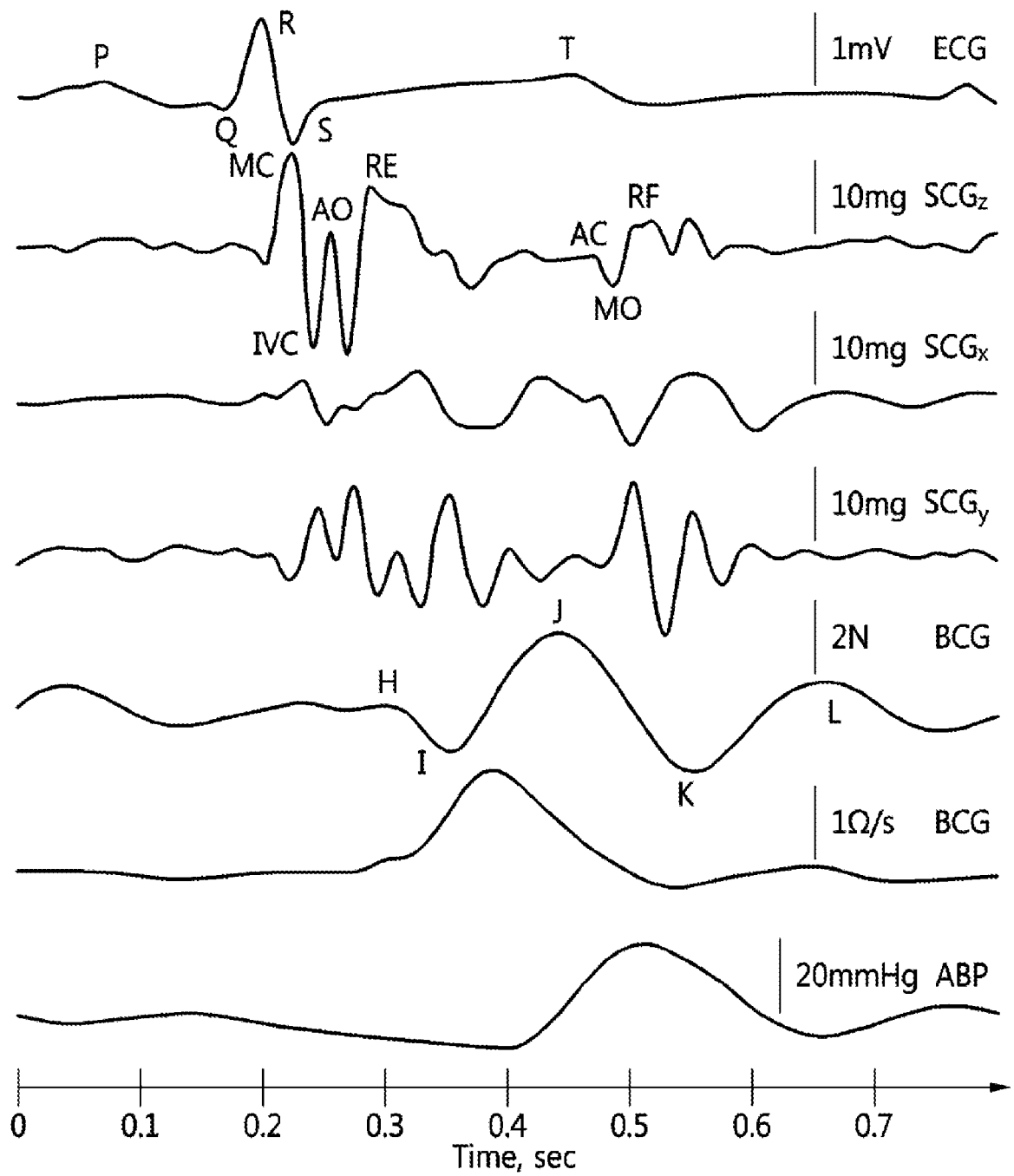
FIG. 5 illustrates an image of a reference image based on a biometric signal of a subject.

FIG. 5 illustrates an image of a reference image based on a biometric signal of a subject.

Referring to FIG. 5, the image monitoring apparatus according to an embodiment of the disclosure may be configured to obtain a plurality of biometric signals over time from an EIT device, and output a corresponding reference image.

As shown in FIG. 5, the image monitoring apparatus according to an embodiment of the disclosure may be configured to display reference images with ECG, SCG, BCG, and arterial blood pressure (ABP) signals based on the received biometric signals.

Thus, the lung ventilation impedance data, the lung ventilation impedance image, the lung perfusion impedance data, the lung perfusion impedance image, and the reference image shown in FIGS. 3A, 3B, 4A, 4B and 5 may be displayed on the image monitoring apparatus according to an embodiment of the disclosure of FIG. 2 based on the physiological and pathological states of the subject.

Figure 6:
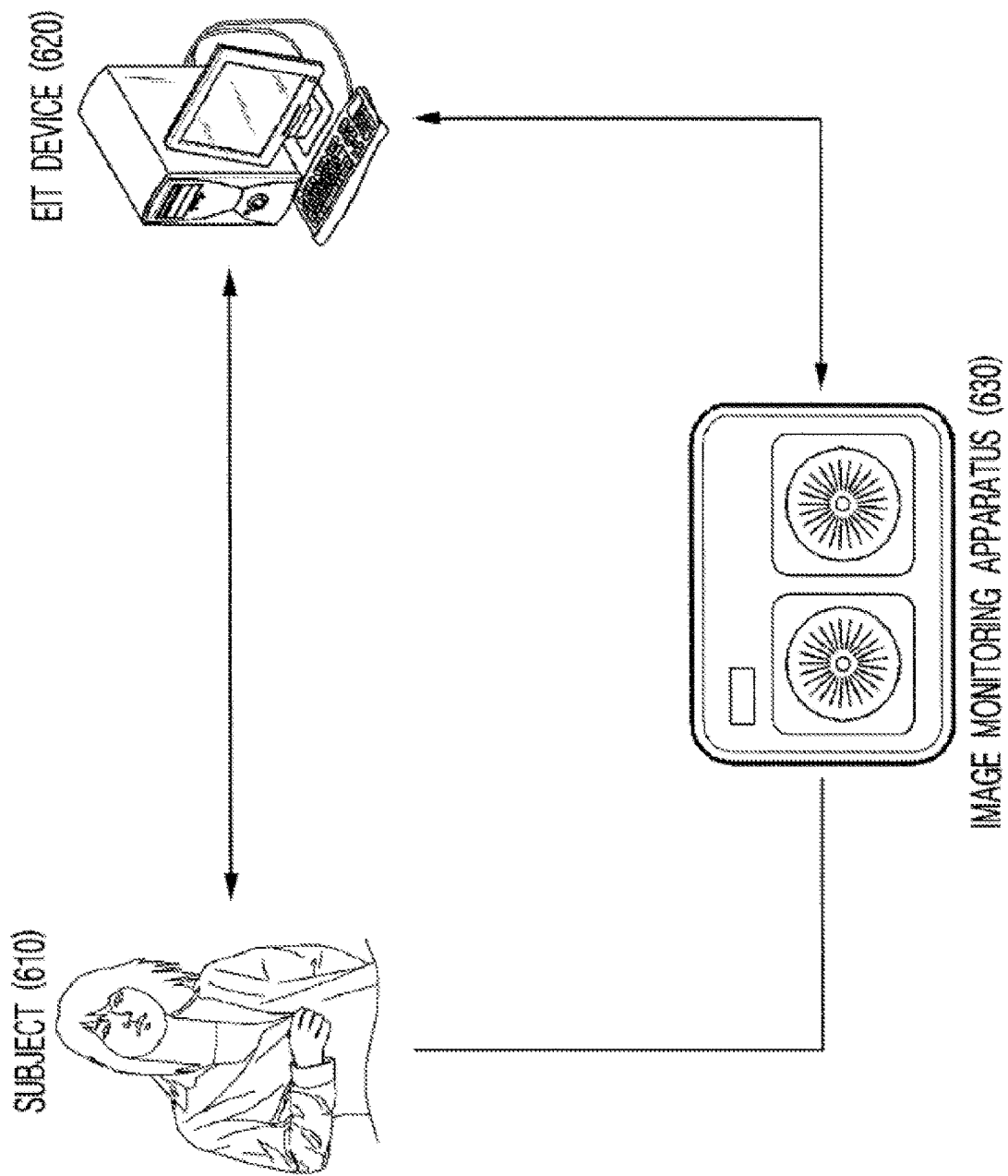
FIG. 6 illustrates an image monitoring system according to an embodiment of the disclosure.

FIG. 6 illustrates an image monitoring system according to an embodiment of the disclosure.

Referring to FIG. 6, an image monitoring system 600 according to an embodiment of the disclosure includes an image monitoring apparatus 630 that receives lung ventilation impedance data, lung perfusion impedance data, bloodstream impedance data and a biometric signal of a subject 610, which are extracted from the EIT device 620, and displays a lung ventilation impedance image, a lung perfusion impedance image, a bloodstream impedance image and a reference image.

To this end, the image monitoring system 600 according to an embodiment of the disclosure includes the EIT device 620 and the image monitoring apparatus 630.

In the image monitoring system according to an embodiment of the disclosure, the EIT device 620 and the image monitoring apparatus 630 may exchange data or a control command through wired/wireless communication.

The EIT device 620 selectively supplies electric currents to at least one pair of electrodes selected among the plurality of electrodes attached along the chest circumference of the subject 610, separates the lung ventilation impedance data and the lung perfusion impedance data according to the impedance data obtained by measuring voltage through unselected electrodes, and the bloodstream impedance data of a heart and blood vessels according to a biometric signal, and senses the biometric signal at a part of the subject 610 targeted to be examined.

Details of the EIT device 620 according to an embodiment of the disclosure will be described later with reference to FIG. 7.

The image monitoring apparatus 630 generates the lung ventilation impedance image, the lung perfusion impedance image and the bloodstream impedance image based on the lung ventilation impedance data, the lung perfusion impedance data and the bloodstream impedance data, and displays at least one of the lung ventilation impedance image, the lung perfusion impedance image, the bloodstream impedance image and the reference image of the sensed biometric signal according to an image, a waveform, and a numerical value.

Thus, the image monitoring apparatus 630 may further include a data receiver (not shown), an image processor (not shown) and a controller (not shown).

The data receiver may be configured to receive the lung ventilation impedance data, the lung perfusion impedance data and the bloodstream impedance data based on the voltage measured at the thorax of the subject 610, which are separated by the EIT device 620, and receive the biometric signal sensed at parts of the subject 610 targeted to be examined.

The image processor may be configured to generate the lung ventilation impedance image, the lung perfusion impedance image and the bloodstream impedance image based on the lung ventilation impedance data, the lung perfusion impedance data and the bloodstream impedance data, and generate the reference image based on the sensed biometric signal.

The controller may be configured to control at least one of the lung ventilation impedance image, the lung perfusion impedance image, the bloodstream impedance image and the reference image based on the physiological and pathological states of the subject 610 to be displayed according to screen modes and parts to be examined.

According to an alternative embodiment, the image monitoring system 600 may be given in a combination form of the image monitoring apparatus 630 and the EIT device 620, but not limited to the example where the image monitoring apparatus 630 and the EIT device 620 are separated as shown in FIG. 6.

Detailed configurations and features of the image monitoring apparatus 630 have been described with reference to FIGS. 1 to 5, and thus repetitive descriptions will be avoided.

Figure 7:
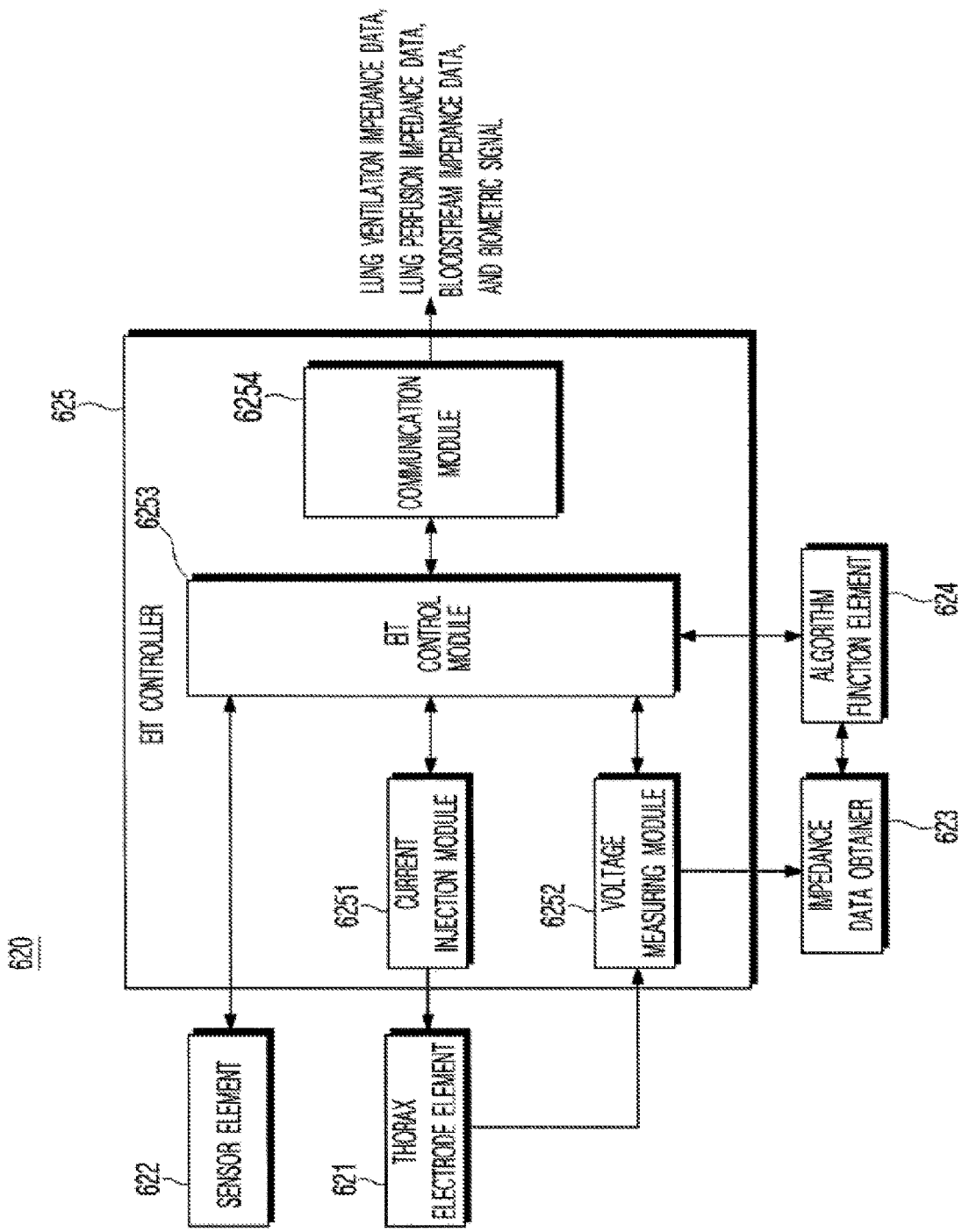
FIG. 7 is a block diagram for describing a configuration of an electrical impedance tomography (EIT) device according to an embodiment of the disclosure.

FIG. 7 is a block diagram for describing a configuration of an EIT device according to an embodiment of the disclosure.

Referring to FIG. 7, the EIT device 620 according to an embodiment of the disclosure selectively supplies electric currents to at least one pair of electrodes selected among the plurality of electrodes attached along the chest circumference of the subject 610, separates the lung ventilation impedance data, the lung perfusion impedance data and the bloodstream impedance data according to the impedance data obtained by measuring the voltages through the unselected electrodes, and senses the biometric signal at parts of the subject 610 targeted to be examined.

To this end, the EIT device 620 according to an embodiment of the disclosure may include a thorax electrode element 621, a sensing element 622, an impedance data obtainer 623, an algorithm function element 624, and an EIT controller 625.

The thorax electrode element 621 is provided with a plurality of electrodes for current injection and voltage detection, and attached along the chest circumference of the subject 610.

The plurality of electrodes may include at least one of the simple electrode or the complex electrode, and may be an EIT electrode attached along the thorax of the subject 610 and measuring the impedance data about the interior of the lung.

The EIT electrodes may be arrayed on one side of a base plate made of a flexible material and attached to the face and neck circumferences of the subject 610.

Further, the EIT electrode is used to inject a low current, which cannot be recognized by the subject 610, for example, a high-frequency current of 1 mA or below, and measure induced voltage. Current-voltage data measured by the EIT electrode may be used to detect a pattern of a thorax (lung) through an imaging algorithm.

The sensing element 622 may be in contact with parts of the subject 610 targeted to be examined and sense the biometric signal.

For example, the sensing element 622 may include a plurality of sensors, which are fiber-based sensors, and perform a function of sensing the biometric signal of the subject 610.

According to an embodiment, the plurality of sensors may be attached to different parts on the body of the subject 610, and the sensing element 622 may be a common name of the plurality of sensors.

According to an embodiment, the sensing element 622 may include at least one of an oxygen-saturation-in-blood sensor for sensing an oxygen saturation in arterial blood ($SpO_2$) signal according to parts of the subject 610 targeted to be examined, a sound sensor for sensing a sound based on biometric activities of the subject 610, a posture sensor for sensing movement of the subject 610, and an ECG sensor for measuring the ECG at parts targeted to be examined.

Here, the oxygen-saturation-in-blood sensor may be attached to the parts of the subject 610 targeted to be examined and sense saturation of peripheral oxygen ($SpO_2$), which is present in hemoglobin among many components of blood.

According to an embodiment, the oxygen-saturation-in-blood sensor may be configured to sense a signal about photoplethysmography (PPG) of a body of the subject 610 based on reflected or transmitted light, and sense the oxygen saturation in blood based on the sensed signal about the PPG.

Further, the sound sensor may be configured to sense at least one sound among breathing, snoring, crying, and sleep-talking. According to an embodiment, the sound sensor may be attached to the parts of the subject 610 targeted to be examined or may be given in a contactless form as being spaced at a predetermined distance from the subject 610 while the subject is sleeping.

Further, the posture sensor may be provided as at least one of a gyro sensor and an acceleration sensor, and attached to the parts of the subject targeted to be examined, thereby sensing the posture, the BCG or the SCG according to the movement of the subject.

Further, the ECG sensor may be in contact with the parts of the subject 610 targeted to be examined, and configured to sense the ECG.

Here, the ECG shows a waveform based on a vector sum corresponding to action potential generated by a special excitatory & conductive system of a heart. In other words, the ECG may refer to a vector sum signal of action potential generated in parts of a heart, i.e. a sinoatrial (SA) node, an atrioventricular (AV) node, a His bundle, a bundle branch, Purkinje fibers, etc. is measured by the electrodes attached to the exterior of the body.

According to an alternative embodiment, the sensing element 622 may be configured to sense at least one of the EEG, the EMG, the EOG, the SCG, and the BCG of the subject 610.

The impedance data obtainer 623 may be configured to obtain impedance data at the thorax of the subject 610 based on voltage measured by the plurality of electrodes.

For example, the impedance data obtainer 623 may obtain a voltage difference signal induced by the injected current through the unselected electrodes among the plurality of electrodes, and obtain the impedance data according to the chest circumference of the subject 610 and the position of the electrode.

The algorithm function element 624 may be configured to separate the lung ventilation impedance data and the lung perfusion impedance data by applying the signal separating algorithm to the obtained impedance data.

For example, the algorithm function element 624 may be configured to separate the lung ventilation impedance data, the lung perfusion impedance data and the bloodstream impedance data varied depending on the blood flow in the heart and major blood vessels by simultaneously applying the sensed biometric signals from the parts of the subject targeted to be examined.

In more detail, the algorithm function element 624 may be configured to separate the lung ventilation impedance data, the lung perfusion impedance data and the bloodstream impedance data by applying the signal separating algorithm to the obtained impedance data, and restore the magnitudes of the separated lung ventilation impedance data, lung perfusion impedance data and bloodstream impedance data.

Below, operations of separating and restoring the impedance data by applying the signal separating algorithm according to an embodiment of the disclosure will be described in detail with reference to FIGS. 11A and 11B.

Figure 11A:
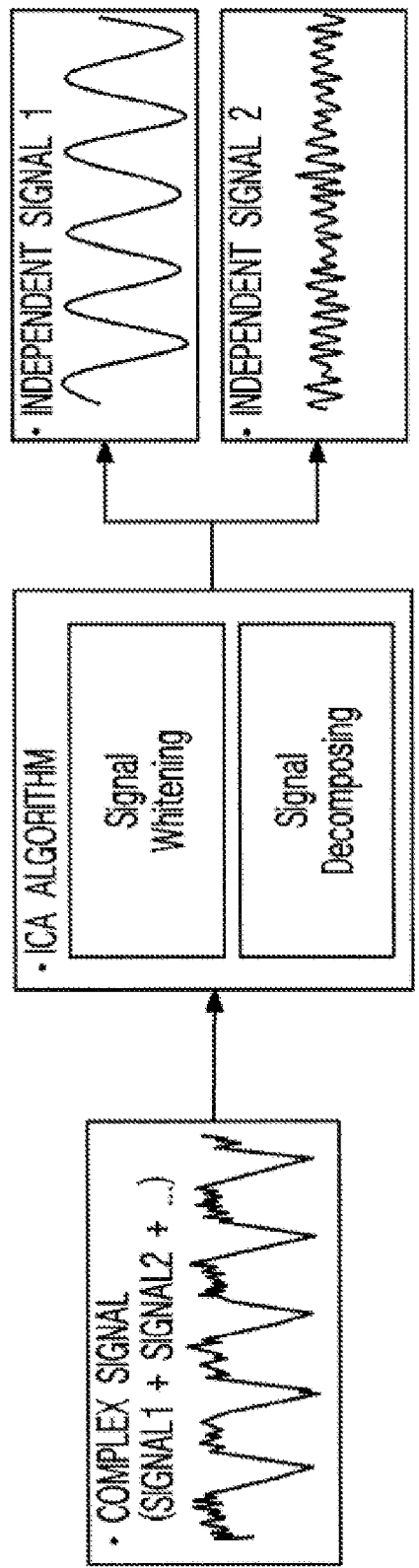
FIGS. 11A and 11B illustrate an example of separating and restoring impedance data by applying a signal separating algorithm according to an embodiment of the disclosure.
Figure 11B:
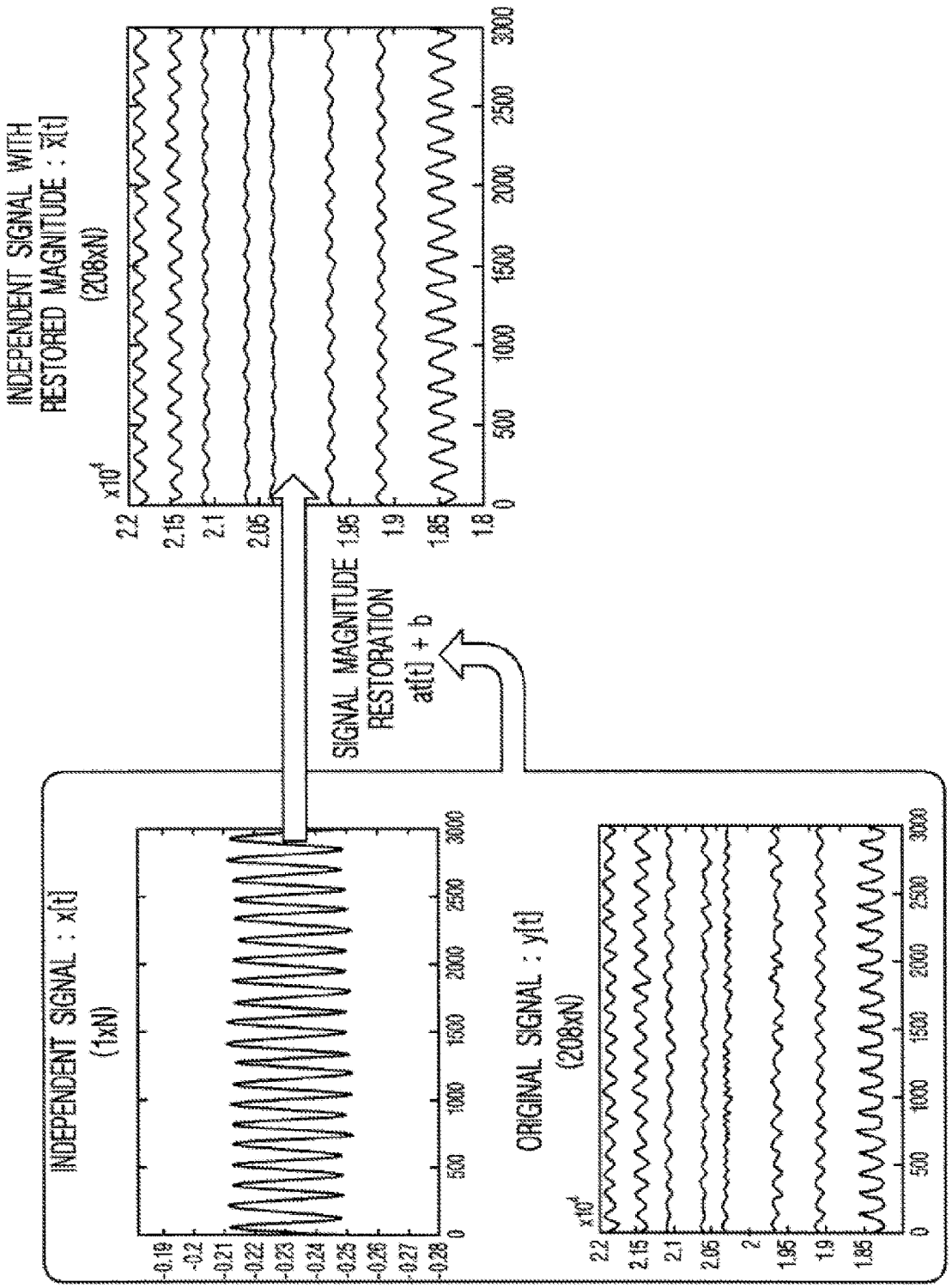

FIGS. 11A and 11B illustrate an example of separating and restoring impedance data by applying a signal separating algorithm according to an embodiment of the disclosure.

In more detail, FIG. 11A illustrates an example that the impedance data is separated by applying the signal separating algorithm, and FIG. 11B illustrates an example that the separated impedance data is restored to have a magnitude of an original signal.

Referring to FIG. 11A, the EIT device 620 according to an embodiment of the disclosure measures the voltage at the chest circumference of the subject 610 through the thorax electrode element 621, and obtains the impedance data through the impedance data obtainer 623.

Thus, the EIT device 620 according to an embodiment of the disclosure receives the impedance data including a combination signal, in which different independent signals are mixed, at the thorax of the subject 610.

In this case, the algorithm function element 624 according to an embodiment of the disclosure may be configured to apply the signal separating algorithm, i.e. ICA algorithm and a simultaneously measured biometric signal to the combination signal, in which various different independent signals are mixed, to thereby separate independent signals respectively corresponding to the lung ventilation impedance data, the lung perfusion impedance data and the bloodstream impedance data.

In more detail, the algorithm function element 624 according to an embodiment of the disclosure may be configured to employ the ICA algorithm for applying signal whitening and signal decomposing to obtain feature information (e.g. the lung ventilation impedance data, the lung perfusion impedance data and the bloodstream impedance data) from the impedance data based on the voltage measured from the chest circumference of the subject 610.

Then, the algorithm function element 624 according to an embodiment of the disclosure may calculate a signal separation matrix, in which independence of signals to be separated by the ICA algorithm is maximized, and use the signal separation matrix to extract the different independent signals from the combination signal.

Referring to FIG. 11B, the algorithm function module 624 according to an embodiment of the disclosure may be configured to calculate a signal magnitude restoration variable between an independent signal and an original signal by applying a signal magnitude restoration algorithm, in order to restore the magnitude of the independent signals separated by the ICA algorithm to the magnitude of the original signal.

Then, the algorithm function element 624 according to an embodiment of the disclosure may use the calculated restoration variable to restore each independent signal of the lung ventilation impedance data, the lung perfusion impedance data and the bloodstream impedance data to have the magnitude of the original signal.

In more detail, the algorithm function element 624 according to an embodiment of the disclosure may be configured to obtain the independent signal ($\tilde{x}[t]$), the magnitude of which is restored by applying the following [Expression 1], i.e. the signal magnitude restoration algorithm to each separated independent signal ($x[t]$).

$$\begin{bmatrix} y_1 \\ y_2 \\ y_3 \\ * \\ * \\ * \\ * \\ y_N \end{bmatrix} = \begin{bmatrix} x_1 1 \\ x_2 1 \\ x_3 1 \\ * \\ * \\ * \\ * \\ x_N 1 \end{bmatrix} \begin{bmatrix} a \\ b \end{bmatrix} \quad \begin{aligned} Y &= X\theta \\ X^T Y &= X^T X \theta \\ (X^T X)^{-1} X^T Y &= \theta \end{aligned} \quad \text{[Expression 1]}$$

$$\underbrace{\phantom{\begin{bmatrix} y_1 \end{bmatrix}}}_{Y} \quad \underbrace{\phantom{\begin{bmatrix} x_1 1 \end{bmatrix}}}_{X} \quad \underbrace{\phantom{\begin{bmatrix} a \end{bmatrix}}}_{\theta}$$

where, a and b indicate signal magnitude restoration variables, x indicate an independent signal, and y indicates an original signal.

Referring back to FIG. 7, the EIT controller 625 of the EIT device 620 according to an embodiment of the disclosure may perform control to selectively supply the currents to at least one pair of electrodes selected among the plurality of electrodes, measure the voltage through the unselected electrodes, and transmit the sensed signal, the lung ventilation impedance data, the lung perfusion impedance data and the bloodstream impedance data.

To this end, the EIT controller 625 according to an embodiment of the disclosure may include a current injection module 6251, a voltage measuring module 6252, and an EIT control module 6253.

The current injection module 6251 may be configured to inject the current having a plurality of frequency ranges through at least one pair of electrodes selected among the plurality of electrodes attached to the thorax of the subject 610.

According to an embodiment, the current injection module 6251 may be configured to select a pair of electrodes and a frequency, generate a voltage signal based on the selected frequency, convert the voltage into an electric current, and inject the converted current to the thorax of the subject 610 through the selected pair of electrodes.

According to an alternative embodiment, the current injection module 6251 may convert the voltage signal into two currents different in phase, correct the two currents to have the same amplitude and frequency, and inject the two corrected currents to the thorax of the subject through the selected pair of electrodes.

The voltage measuring module 6252 may be configured to measure voltages induced by the currents injected through the unselected electrodes among the plurality of electrodes among the plurality of second electrodes.

For example, the voltage measuring module 6252 may be configured to remove noise included in detected voltage based on the slope of the measured voltage, and replace a voltage corresponding to a section, a level of which is greater than a preset threshold, by a preset voltage when the slope of the detected voltage is higher than the threshold.

The EIT control module 6253 may be configured to control selection of at least one pair of electrodes from the plurality of electrodes, control selection of the unselected electrodes, and control sensing of the sensing element 622 to be in contact with the parts of the subject 610 targeted to be examined. Further, the EIT measurement may be controlled in sync with a certain time of a waveform of a signal measured by the biometric signal sensing element 622.

For example, the EIT control module 6253 may be configured to control the current injection module 6251 to measure the impedance data at the thorax of the subject 610.

Further, the EIT control module 6253 may control the voltage measuring module 6252 and the impedance data obtainer 623 to measure vertical and horizontal impedance data with regard to the thorax of the subject 610, and control the algorithm function element 624 to separate the lung ventilation impedance data, the lung perfusion impedance data and the bloodstream impedance data from the measured impedance data.

Further, the EIT control module 6253 may be configured to control a communication module 6254 to transmit the lung ventilation impedance data, the lung perfusion impedance data, the bloodstream impedance data and the biometric signal through wired/wireless communication.

In terms of obtaining the lung ventilation impedance data, the lung perfusion impedance data and the bloodstream impedance data of the subject by the EIT device 620 according to an embodiment of the disclosure, the EIT method is as follows.

The EIT controller 625 according to an embodiment of the disclosure selects channel and sinusoidal frequencies in response to a command, and selects a pair of electrodes in the thorax electrode element 621 corresponding to the selected channel. The selected pair of electrodes are used for injecting the current to the thorax of the subject 610, and the unselected electrodes are used for measuring the voltage on the subject 610.

When the channel and sinusoidal frequencies are selected, the EIT controller 625 outputs a control signal for controlling a field programmable gate array (FPGA, not shown). The control signal may include information about the selected frequencies.

The FPGA is configured to receive and store the control signal, and generate a sinusoidal voltage signal based on the received control signal. In particular, the FPGA is configured to generate a voltage signal based on frequency information included in the control signal, and transmits the generated voltage signal to two 16 bit D/A converters (not shown). In this case, the FPGA controls a 8 bit D/A converter (not shown) to adjust the amplitude of the voltage signal transmitted to the 16 bit D/A converter. Then, the voltage signals output to the two 16 bit D/A converters are converted into electric currents by the voltage—the current converters (not shown), and the two currents are transmitted to a corrector (not shown). The corrector (not shown) adjusts the two currents to have the same amplitude and frequency. Here, there is a phase difference of 180° between the two currents.

In addition, the EIT control module 6253 of the EIT controller 625 controls the current injection module 6251 to transmit two currents passed through the corrector to the pair of electrodes selected in the thorax electrode element 621.

The currents injected to the chest circumference of the subject 610 causes the surface thereof to induce voltages different in level according to resistivity or conductivity of internal tissues. When the electrodes unselected in the thorax electrode element 621 senses the voltages on the surface of the chest circumference of the subject 610, the voltage measuring module 6252 receives the voltages on the surfaces corresponding to the unselected electrodes.

Then, the voltage measuring module 6252 determines whether the surface voltage data includes noise based on the slope of the sensed surface voltage data, and then replaces the corresponding voltage data by another voltage level when the surface voltage data includes the noise. Further, the EIT control module 6253 adjusts a gain of the voltage amplifier (not shown) according to the maximum level of the voltage data. For example, the EIT control module 6253 does not adjust the gain of the voltage amplifier when the maximum level of the voltage data reaches 90% of the maximum output of the A/D converter (not shown), but increases the gain of the voltage amplifier when the maximum level of the voltage data does not reach 90% of the maximum output of the A/D converter.

When the noise is removed from the voltage data and the gain of the voltage amplifier is adjusted, the voltage measuring module 6252 amplifies the voltage data according to the adjusted gain and the A/D converter converts the voltage data into a digital value.

Then, the impedance data obtainer 623 processes the voltage data in consideration of gain information according to channels, based on the channel information and the gain information. When the detected voltage data different in gain is directly used, it is difficult to accurately represent electric characteristics inside the thorax of the subject 610. Therefore, the corresponding voltage level has to be decreased or increased according to the gain. For example, when a gain value is greater than a reference gain value, the corresponding voltage level is decreased and multiplied by a ratio of the gain value to the reference gain value.

Thus, the impedance data obtainer 623 may be configured to process the voltage data in consideration of the gain information according to the channels, and then obtain the impedance data based on the voltage data.

Then, the algorithm function element 624 may be configured to separate the lung ventilation impedance data, the lung perfusion impedance data and the bloodstream impedance data from the impedance data, and the EIT control module 6253 may transmit the lung ventilation impedance data, the lung perfusion impedance data and the bloodstream impedance data through the communication module 6254.

According to an embodiment, the EIT device 620 may transmit the separated lung ventilation impedance data, lung perfusion impedance data and bloodstream impedance data to the image monitoring apparatus 630. According to an alternative embodiment, the lung ventilation impedance image, the lung perfusion impedance image and the bloodstream impedance image of the subject 610 based on the lung ventilation impedance data, the lung perfusion impedance data and the bloodstream impedance data may be provided to the image monitoring apparatus 630.

Alternatively, there may be various methods of generating an image of an inside of a measurement target (e.g. a thorax) based on the voltage data on the surface of the thorax of the subject.

Further, the EIT device 620 may provide the sensed biometric signal to the image monitoring apparatus 630, but may alternatively provide the reference image of the biometric signal.

Figure 8A:
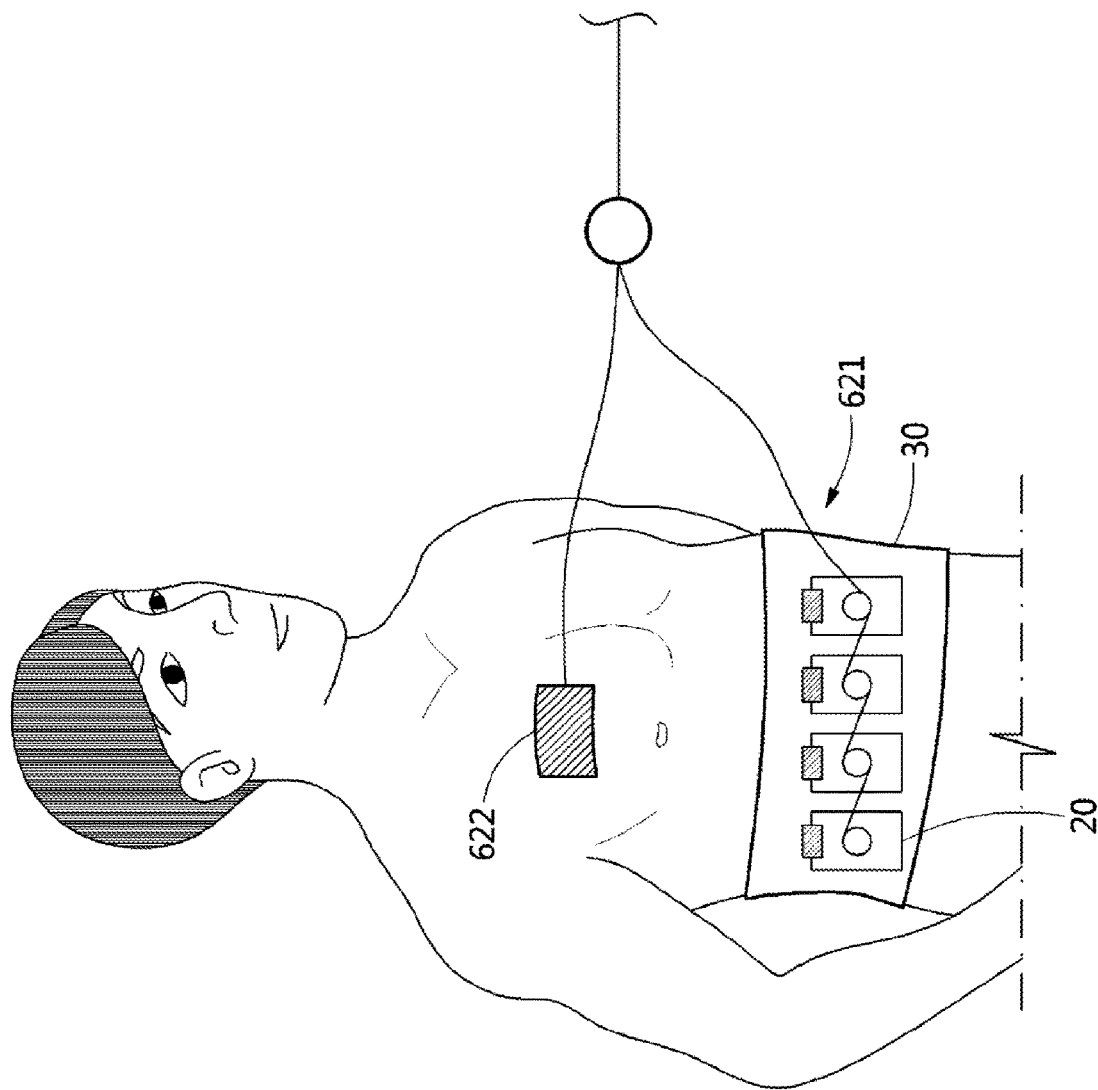
FIG. 8A illustrates an application of an EIT device according to an embodiment of the disclosure, and FIG. 8B schematically illustrates a thorax electrode element.
Figure 8B:
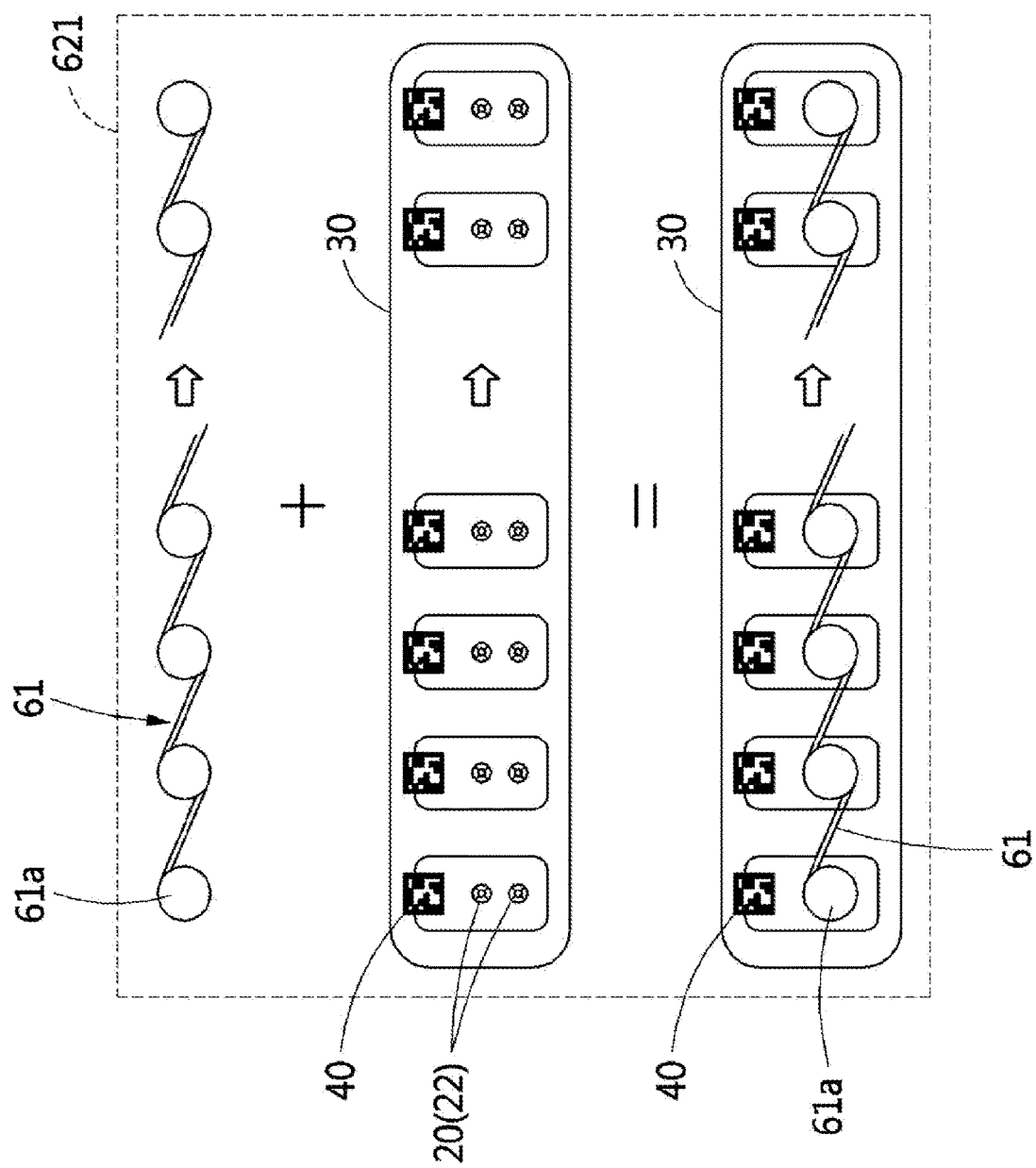

FIG. 8A illustrates an application of an EIT device according to an embodiment of the disclosure, and FIG. 8B schematically illustrates a thorax electrode element.

Referring to FIG. 8A, the EIT device 620 according to an embodiment of the disclosure includes the thorax electrode element 621 attachable to the thorax of the subject 610, and the sensing element 622 attached to the parts of the subject 610 targeted to be examined.

The thorax electrode element 621 attached to the chest circumference of the subject 610 includes the plurality of electrodes 20, and the plurality of electrodes 20 may be formed on the base plate 30 at regular intervals to measure the impedance data based on the shape of the lung according to the respiration of the subject 610.

According to an embodiment, the base plate 30 is not necessarily limited to a shape of a belt-type array electrode. Alternatively, the base plate 30 may be a base plate 30 including the plurality of electrodes 20, an array of which has at least one pattern or structure among a vest type, a belt type, and a patch type, by taking contact strength for enhancing a data measurement level into account while minimizing pressure that the subject feels.

For example, the plurality of electrodes 20a may include conductive fiber electrodes manufactured based on silver (Ag)-plated elastic fiber or polymer nanofiber web (PVDF), but be not limited thereto. Alternatively, the electrodes may be made of various materials having less reaction with skin even against long-time measurement.

In FIG. 8A, a plurality of electrodes 20 in the thorax electrode element 621 according to an embodiment of the disclosure may be formed on a base plate 30 at regular intervals or may be arranged with various arrays and structures on the parts (e.g. the thorax) targeted to be examined according to the features and purposes. Further, the base plate 30 may have a certain length and area in order to measure impedance data while surrounding the parts targeted to be examined, such as the thorax or the abdomen of the subject 610, but there are no limits to the length and the area. Alternatively, the length and the area may be varied depending on embodiments.

The thorax electrode element 621 may effectively measure distribution of an electric field around the surfaces of the thorax based on change in an electrode array structure and a measurement structure in such a manner that the plurality of electrodes 20 are arranged in the form of a 2D or 3D array as attached to the thorax of the subject 610.

According to an embodiment, the thorax electrode element 621 to be formed on the base plate 30 are arranged in the 3D array and configured to measure impedance data corresponding to a layer, thereby leading to a more accurate and effective diagnosis than that of a conventional method of providing only a 2D cross-section image at a certain position.

The sensing element 622 may contact any part of the subject 610 targeted to be examined, and therefore the position and number of parts targeted to be in contact are not limited to those shown in FIG. 8A.

The sensing element 622 may include at least one of the sound sensor, the posture sensor and the biometric signal measuring sensor, and may be a fiber-based sensor to be attached to the body of the subject. Further, the sensing element 622 may refer to a plurality of sensors.

According to an embodiment, the plurality of sensors may be attached to different parts on the body of the subject 610, and the sensing element 622 may be a common name of the plurality of sensors.

For example, the sensing element 622 may be configured to sense the biometric signal including at least one among $SpO_2$, PPG, ECG, EEG, EMG, EOG, SCG, BCG and ABP.

Referring to FIG. 8B, the thorax electrode element 621 according to an embodiment of the disclosure include a plurality of electrodes 20, and are mountable along the chest circumference of the subject 610 to be examined. To this end, the thorax electrode element 621 includes the base plate 30 (hereinafter, referred to as an electrode belt) provided with the plurality of electrodes 20.

Below, the electrode belt with the plurality of electrodes 20 will be described in detail with reference to FIGS. 9A and 9B.

Figure 9A:
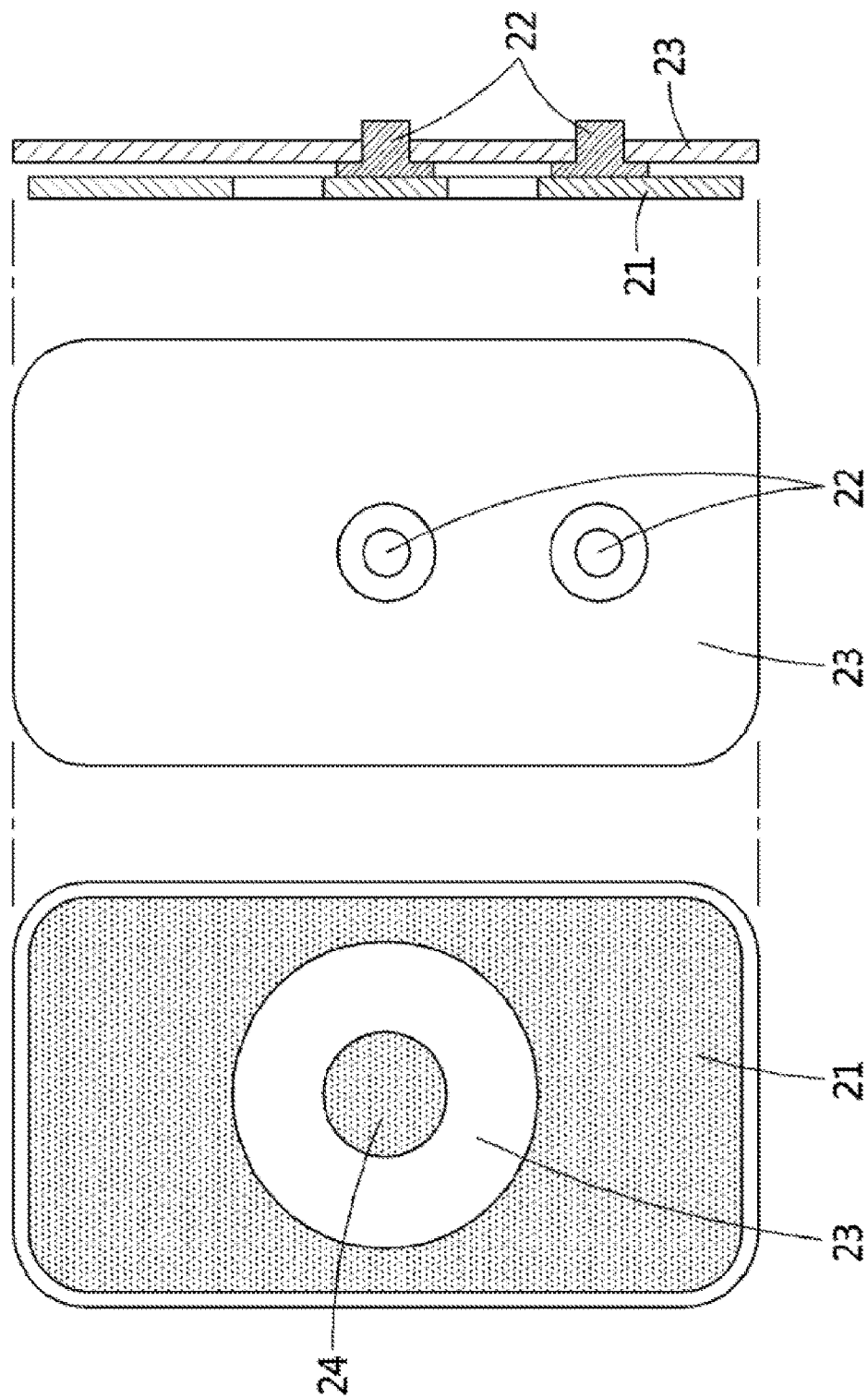

FIGS. 9A and 9B schematically illustrate a complex electrode employed in the EIT device shown in FIG. 8B.

Referring back to FIG. 8B, a cable belt 61 is connected to a connector 22 exposed through an electrode installation hole 31 in which the plurality of electrodes 20 (hereinafter, referred to as the complex electrode) is installed. In this case, the cable belt 61 may include a plurality of connection cable terminals 61a for injecting the currents, corresponding to the complex electrodes 20.

Thus, the voltage measuring module 6252 measures the voltage induced by the current injected to the complex electrode 20 through the cable belt 61. Specifically, the EIT device 620 according to an embodiment of the disclosure generates the currents having multiple frequencies through the cable belt 61 and applies the generated currents to the complex electrode 20 of the electrode belt 30 put on the subject 610 while controlling the amplitude and phase of the current. In this case, the currents having multiple frequencies are injected through a first electrode 21 of the complex electrode 20, and a voltage difference signal induced by the injected current is obtained through a second electrode 24 of the complex electrode 20.

Referring to FIG. 9A, the complex electrode 20 includes the first electrode 21 made of a conductive material for injecting a current, the second electrode 24 made of a conductive material for measuring a voltage, and a connector 22 shaped like a button to be connected to the cable belt 61. The first electrode 21 injects the current through a relatively large area as compared with the second electrode 24, and the second electrode 24 measures the voltage through a relatively small area as compared with the first electrode 21 and forms a pair with the second electrode 24 of the repetitive complex electrodes 20 on the cable belt 61.

In this case, the first electrode 21 is shaped like a flat plate, and the connector 22 shaped like a button is provided in the form of a pair of projections which protrude as being connected to the first electrode 21 and the second electrode 24. The first and second electrodes 21 and 24 of each of the plurality of complex electrodes 20 are installed with a nonconductor 23 made of a nonconductive material therebetween in the electrode belt 30.

The foregoing example illustrates that the plurality of electrodes 20 includes the complex electrode, but the plurality of electrodes 20 is not limited to this example. As an alternative example, the simple electrode 20' as shown in FIG. 9B is also possible. In a case of the simple electrode 20', the injection of the current or the measurement of the voltage is performed in a single conductive electrode 21' which is supported on a nonconductor 22'.

Further, the electrode 20 or 20' may be made of a flexible conductive fiber or a conductive polymeric material, and may be given in the form of a dry-type electrode.

Figure 10A:
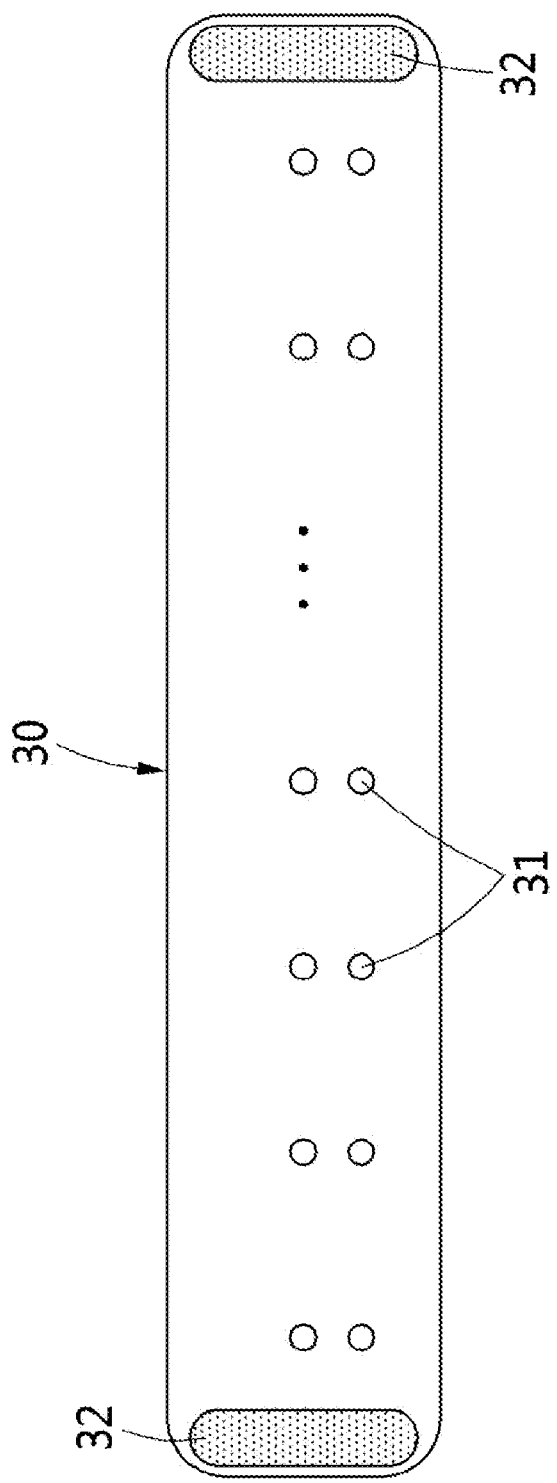
FIGS. 10A to 10D schematically illustrate an electrode belt.
Figure 10B:
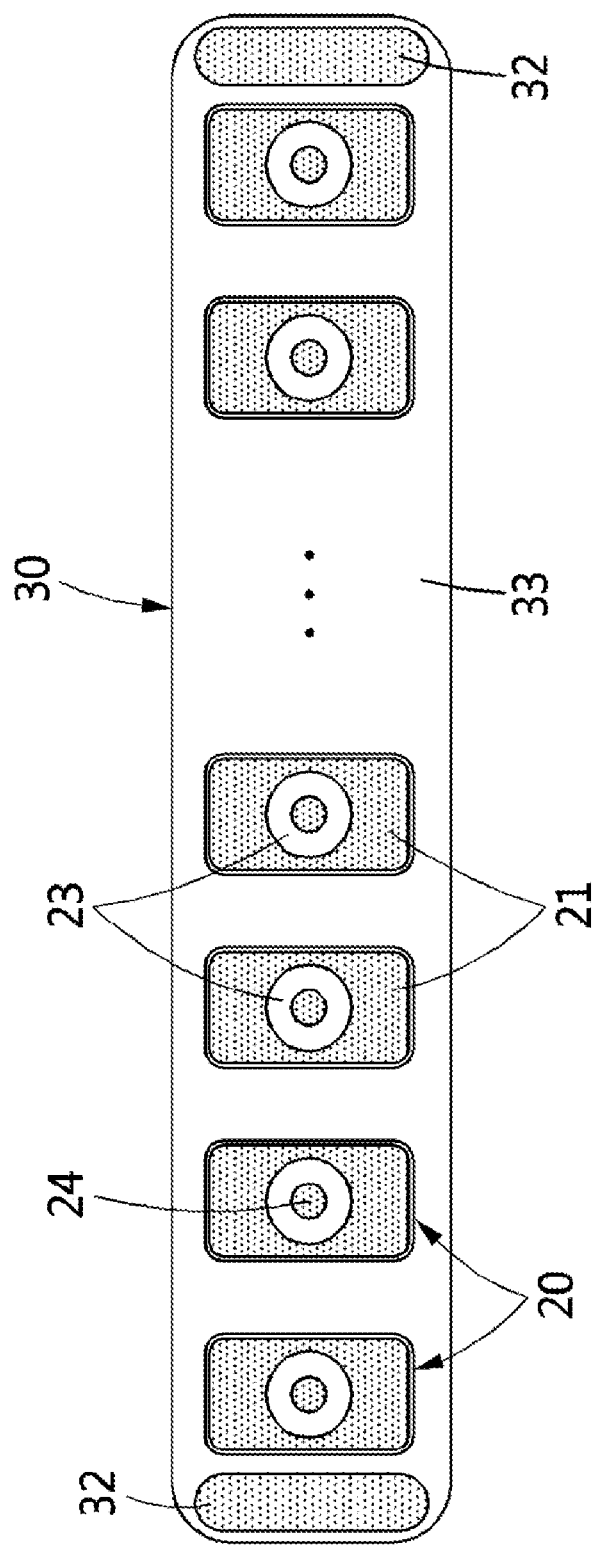
Figure 10C:
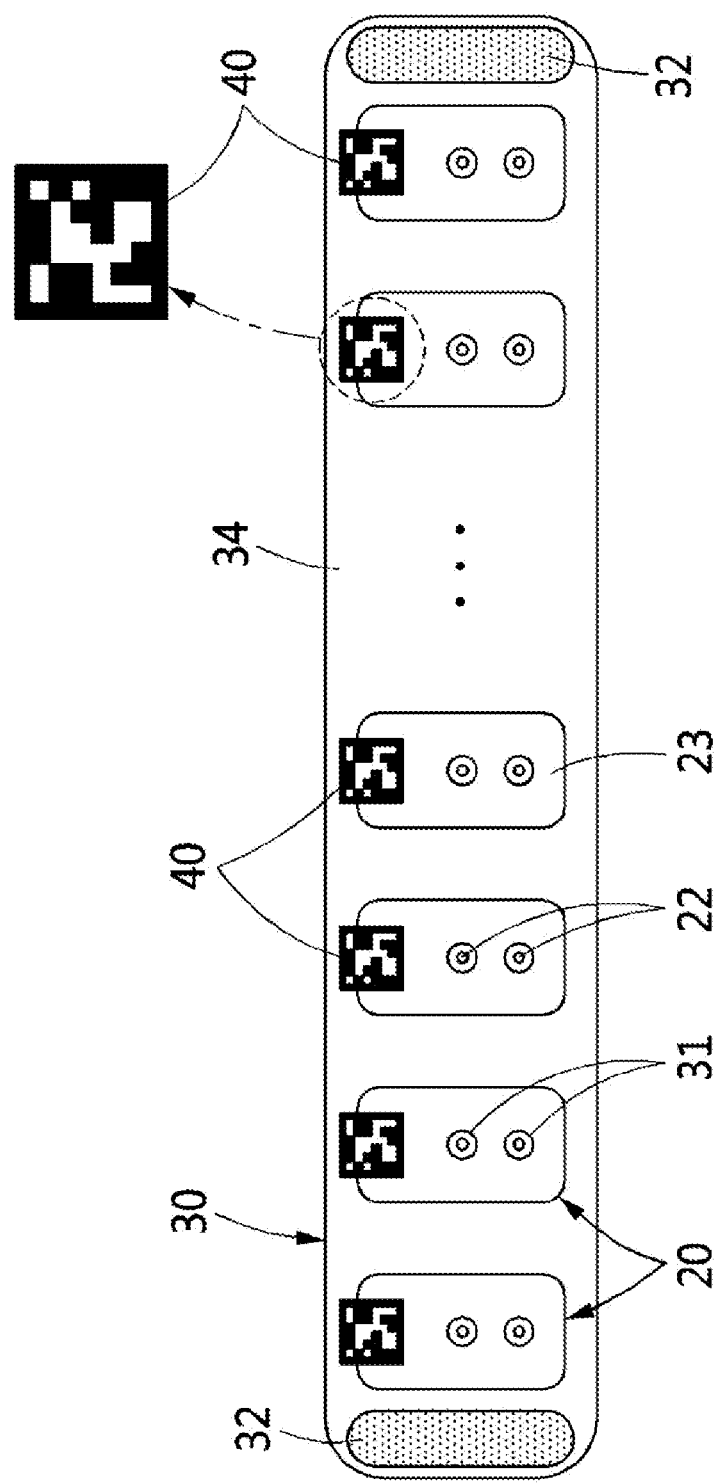
Figure 10D:
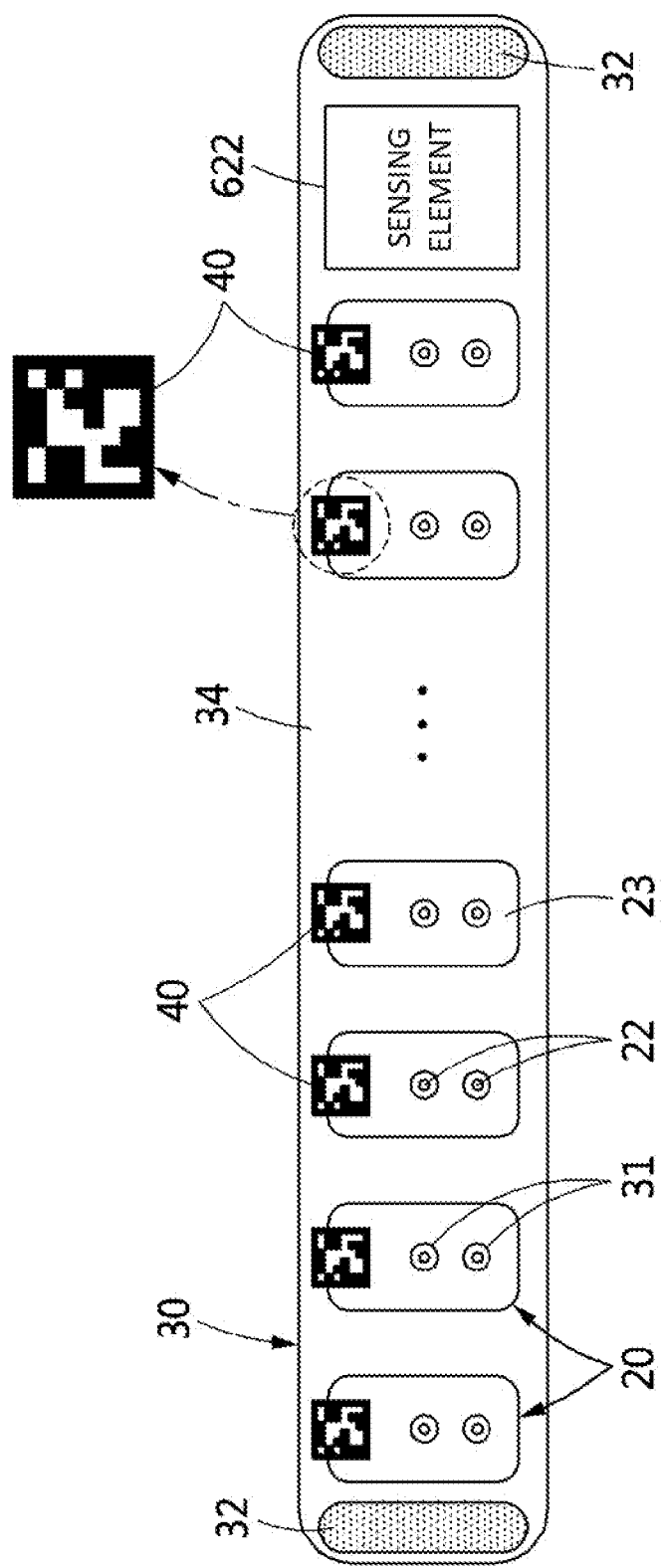
Figure 10E:
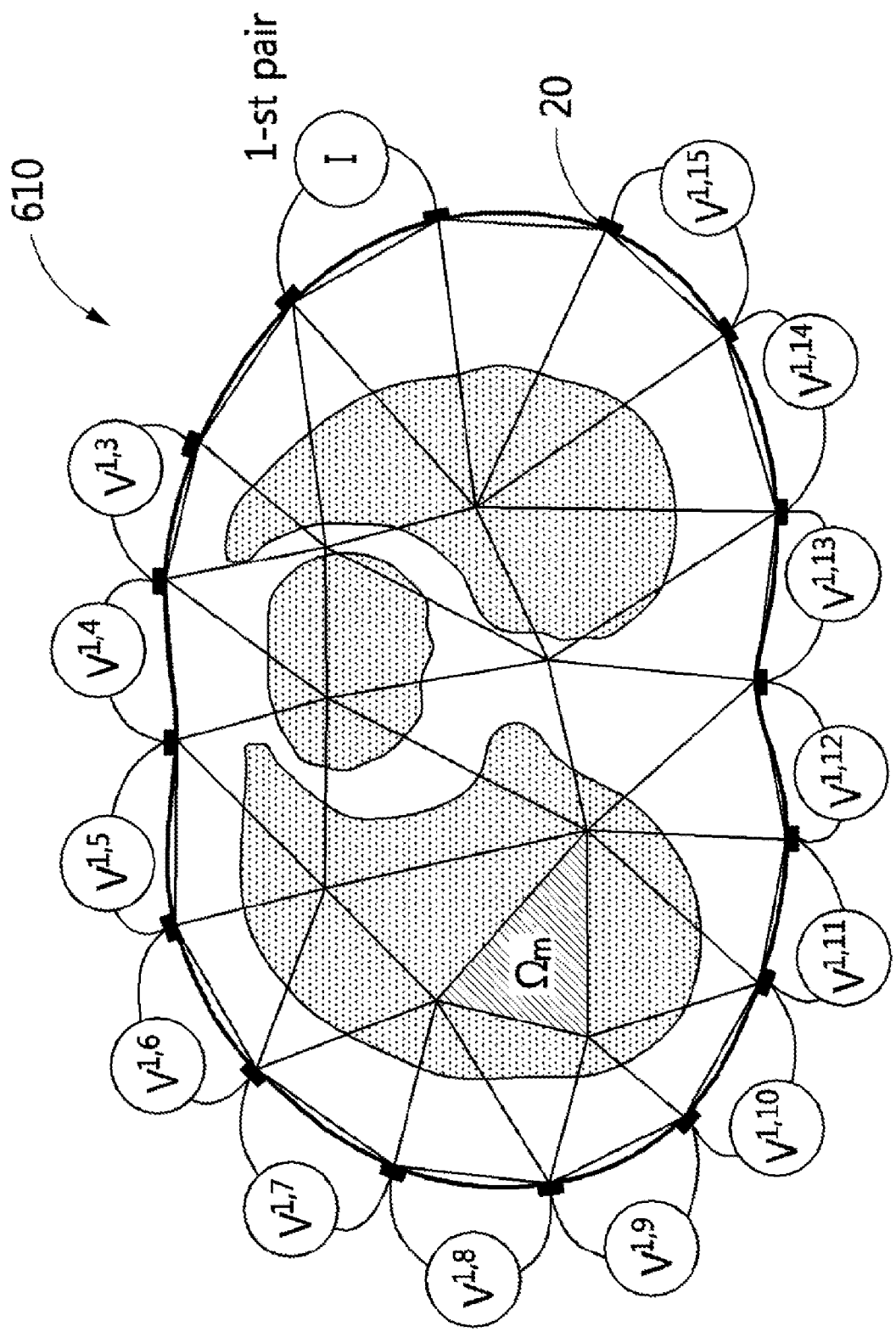
FIG. 10E illustrates an example that the electrode belt is attached to a body of a subject.

FIGS. 10A to 10D schematically illustrate an electrode belt, and FIG. 10E illustrates an example that the electrode belt is attached to a body of a subject.

Referring to FIG. 10A, the electrode belt 30 is made of an elastic material such as fiber, silicon and the like polymeric compound, and the number of provided electrode installation holes 31 and the number of installed complex electrodes 20 may be variable. Meanwhile, the electrode belt 30 is provided with a pair of fasteners 32 at opposite ends thereof, which are fastened to each other and maintain the electrode belt 30 as wound around the body of the subject 610.

This embodiment of the disclosure illustrates that the electrode belt 30 is wound around parts, i.e. the chest circumference of the subject 610 targeted to be examined, and fastened by Velcro type fasteners 32 provided at the opposite ends thereof. Alternatively, without limitations, one of various fasteners such as hook types, etc. may be employed as the fasteners 32.

The electrode belt 30 includes a contact surface 33 to be in contact with the subject 610 while having the plurality of complex electrodes 20 as shown in FIG. 10B, and an exposure surface 34 to be exposed to the EIT controller 625 according to an embodiment of the disclosure while being opposite to the contact surface 33 as shown in FIG. 10C. In this case, the first electrode 21 and the second electrode 24 of the complex electrode 20 are exposed on the contact surface 33 of the electrode belt 30, and the connector 22 connected to the cable belt 61 is exposed through the electrode installation hole 31 on the exposure surface 34. In addition, the exposure surface 34 of the electrode belt includes a plurality of indicators 40, i.e. markers respectively corresponding to the plurality of complex electrodes 20 and having a plurality of colors and patterns corresponding to information of each of the plurality of complex electrodes 20.

According to an embodiment, the indicators 40, i.e. the markers may be different in shape according to the complex electrodes 20, and include corresponding channel numbers or pieces of data information different from one another, so that the position of the electrode can be identified as the indicator 40 is recognized (sensed).

Referring to FIG. 10D, the electrode belt 30 may further include the sensing element 622 to be attached to the parts of the subject 610 targeted to be examined, and thus be, together with the sensing element 622, attached to the skin of the subject 610.

The sensing element 622 will not be described because the features thereof are described above.

Referring to FIG. 10E, the complex electrodes 20 included in the electrode belt are arranged in the form of the 3D array along the body circumference of the subject 610 to be examined, and it is thus possible to obtain a 3D image at a certain position (a thorax, an abdomen or an upper airway) because impedance corresponding to each layer is measurable by injecting the currents through the selected pair of electrodes and measuring the voltage induced by the injected currents.

Figure 12:
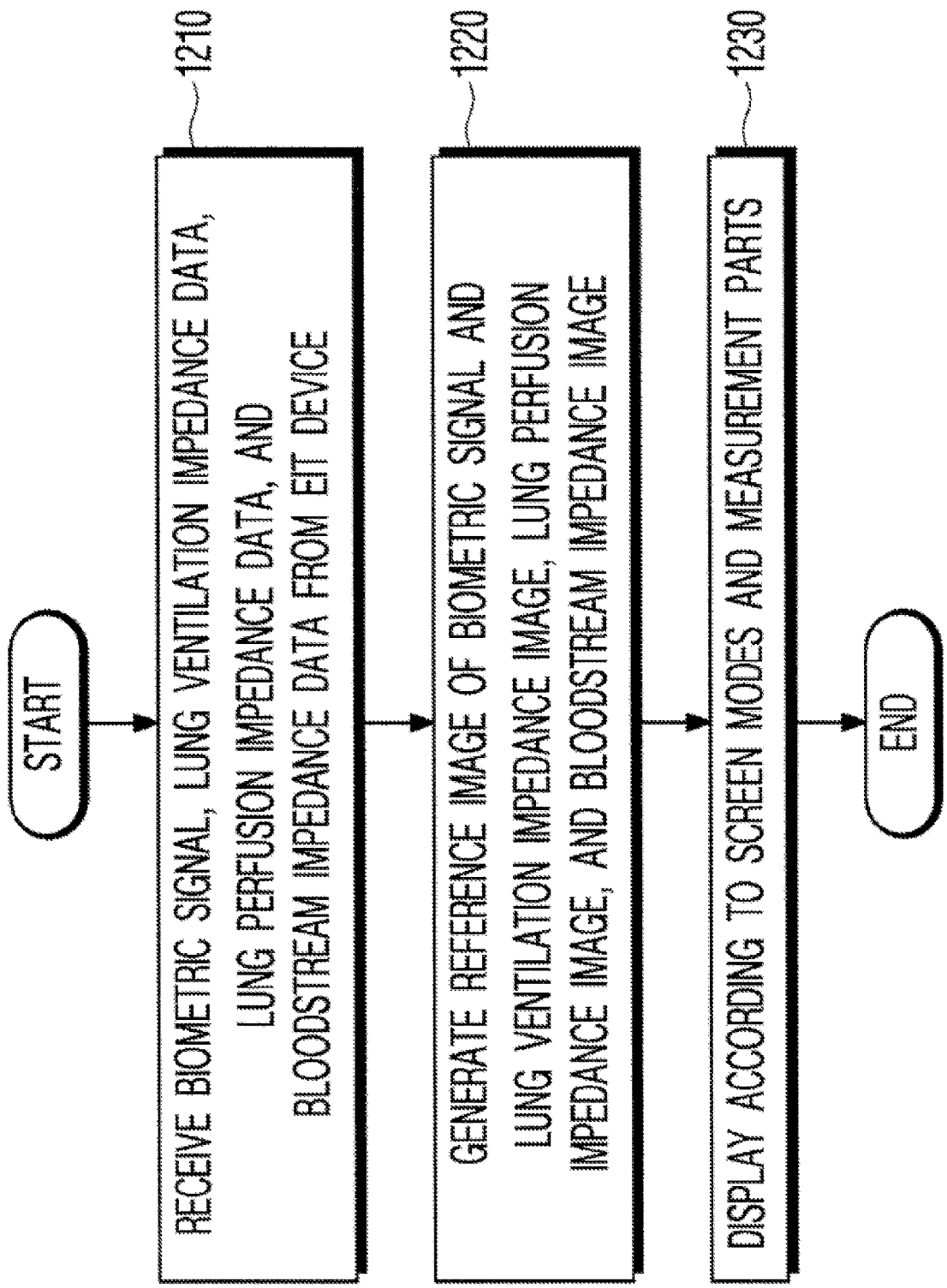
FIG. 12 is a flowchart showing a method of monitoring a state of a subject in real time through an image monitoring apparatus according to an embodiment of the disclosure.

FIG. 12 is a flowchart showing a method of monitoring a state of a subject in real time through an image monitoring apparatus according to an embodiment of the disclosure.

Referring to FIG. 12, at operation 1210, the lung ventilation impedance data, the lung perfusion impedance data and the bloodstream impedance data based on the voltage measured at the thorax of the subject and separated by the EIT device are received, and the biometric signal sensed at parts of the subject targeted to be examined is received.

At operation 1220, the lung ventilation impedance image, the lung perfusion impedance image and the bloodstream impedance image are generated based on the lung ventilation impedance data, the lung perfusion impedance data and the bloodstream impedance data, and the reference image is generated based on the sensed biometric signal.

The operation 1220 may include operation of restoring the lung ventilation impedance image and the lung perfusion impedance image of conductivity and permittivity images about the interior of the thorax of the subject and the bloodstream impedance data related to blood flow in a heart and major blood vessels from the lung ventilation impedance data, the lung perfusion impedance data and the bloodstream impedance data, respectively.

Thus, the operation 1220 include operation of quantifying at least one of change, degree and pattern of ventilation inside a lung over time based on the lung ventilation impedance image and the lung perfusion impedance image, and quantifying at least one of dynamic bloodstream change, degree and pattern in a heart and blood vessels over time based on the bloodstream impedance images.

Further, the operation 1220 may include operation of calculating at least one of average deviation, average variation, average phase delay, and an average absolute impedance value in the lung ventilation impedance image, the lung perfusion impedance image, the bloodstream impedance image and the reference image.

Further, the operation 1220 may include operation of generating the reference image including the waveform and the numerical value with regard to time based on the sensed biometric signal, and calculate at least one of the average deviation, the average variation and the average phase delay of the biometric signal.

The operation 1220 may include operation of collectively analyzing and processing the impedance images measured in sync with features of the biometric signal related to the sensed cardiopulmonary function.

At operation 1230, at least one of the lung ventilation impedance image, the lung perfusion impedance image, the bloodstream impedance image and the reference image based on the physiological and pathological states of the subject is displayed according to the screen modes and measurement parts.

The method according to the embodiments may be actualized in the form of program instructions to be implemented through various computing means, and recorded in a computer readable medium. The computer readable medium may include a program instruction, a data file, a data structure solely or in combination. The program instructions recorded in the medium may be specially designed and configured for the embodiments or may be available as publicly known to a person having an ordinary skill in the art of computer software. The computer readable medium may for example include a hard disk, a floppy disk, a magnetic tape and the like magnetic media; a CD-ROM, a DVD and the like optical media; a floptical disk and the like magneto-optical media; and a ROM, a RAM, a flash memory and the like hardware device specially configured to store and implement a program instruction. The program instruction may for example include not only a machine code produced by a compiler, but also a high-level language to be implemented by a computer through an interpreter or the like. The hardware device may be configured to operate as one or more software modules to carry out the operations of the embodiment, and vice versa.

Although few embodiments are described with restricted examples and drawings, various modifications and changes can be made in the embodiments by a person having an ordinary skill in the art. For example, suitable results may be achieved even if the described techniques are performed in a different order, and/or if components in a described system, architecture, device, or circuit are combined in a different manner and/or replaced or supplemented by other components or their equivalents.

Therefore, other realizations, other embodiments and equivalents to claims may also belong to the scope of appended claims.

The invention claimed is:

1. An image monitoring apparatus comprising:
a data receiver configured to receive at least one of lung ventilation impedance data, lung perfusion impedance data, and bloodstream impedance data, which are separated from voltage measured at a thorax of a subject by an electrical impedance tomography (EIT) device;
an image processor configured to generate at least one of a lung ventilation impedance image, a lung perfusion impedance image and a bloodstream impedance image based on the lung ventilation impedance data, the lung perfusion impedance data and the bloodstream impedance data, respectively; and
a controller configured to control at least one of the lung ventilation impedance image, the lung perfusion impedance image, and the bloodstream impedance image to be displayed according to screen modes and measurement parts,
wherein the measured voltage is separated into the lung ventilation impedance data, the lung perfusion impedance data, and the bloodstream impedance data prior to generating the lung ventilation impedance image, the lung perfusion impedance image, and the bloodstream impedance image.

2. The image monitoring apparatus according to claim 1, wherein the image processor generates at least one of the lung ventilation impedance image, the lung perfusion impedance image and the bloodstream impedance image based on change and time delay in at least one of the lung ventilation impedance data, the lung perfusion impedance data and the bloodstream impedance data.

3. The image monitoring apparatus according to claim 1, wherein the image processor quantifies at least one of change, degree of the change and pattern of the change in an interior of a lung over time based on the lung ventilation impedance image and the lung perfusion impedance image, and quantifies at least one of dynamic bloodstream change, degree of the change and pattern of the change in a heart and blood vessels over time based on the bloodstream impedance image.

4. The image monitoring apparatus according to claim 1, wherein the image processor calculates at least one of average deviation, average variation, average phase delay and an average absolute impedance value in at least one of the lung ventilation impedance image, the lung perfusion impedance image, and the bloodstream impedance image.

5. The image monitoring apparatus according to claim 4, wherein the controller controls at least one of the lung ventilation impedance image, the lung perfusion impedance image, and the bloodstream impedance image, which have been quantified, based on a pathological state of the subject to be displayed according to the preset and classified screen modes or measurement parts.

6. The image monitoring apparatus according to claim 1, wherein the EIT device comprises:

a thorax electrode element provided with a plurality of electrodes for current injection and voltage detection, and attached along a chest circumference of a subject to be examined;
an impedance data obtainer configured to obtain impedance data about the thorax of the subject based on the voltage measured through the plurality of electrodes;
an algorithm function element configured to separate the lung ventilation impedance data, the lung perfusion impedance data, and the bloodstream impedance data by applying a signal separating algorithm to the obtained impedance data; and
an EIT controller configured to selectively supply electric currents to at least one pair of electrodes selected among the plurality of electrodes, measure voltage through unselected electrodes, and control the lung ventilation impedance data, the lung perfusion impedance data and the bloodstream impedance data to be transmitted.

7. An image monitoring system comprising:
an electrical impedance tomography (EIT) device configured to selectively supply electric currents to at least one pair of electrodes selected among a plurality of electrodes attached along a chest circumference of a subject, separate at least one of lung ventilation impedance data, lung perfusion impedance data and bloodstream impedance data, which are based on impedance data obtained by measuring voltage through unselected electrodes; and
an image monitoring apparatus configured to display at least one of a lung ventilation impedance image, a lung perfusion impedance image, a bloodstream impedance image based on at least one of the lung ventilation impedance data, the lung perfusion impedance data and the bloodstream impedance data,
wherein the measured voltage is separated into the lung ventilation impedance data, the lung perfusion impedance data, and the bloodstream impedance data prior to generating the lung ventilation impedance image, the lung perfusion impedance image, and the bloodstream impedance image.

8. The image monitoring system according to claim 7, wherein the image monitoring apparatus comprises:
a data receiver configured to receive at least one of the lung ventilation impedance data, the lung perfusion impedance data and the bloodstream impedance data, which are separated from voltage measured at a thorax of the subject by the EIT device;
an image processor configured to generate at least one of the lung ventilation impedance image, the lung perfusion impedance image and the bloodstream impedance image based on at least one of the lung ventilation impedance data, the lung perfusion impedance data and the bloodstream impedance data; and
a controller configured to control at least one of the lung ventilation impedance image, the lung perfusion impedance image, and the bloodstream impedance image to be displayed according to screen modes and measurement parts.

9. The image monitoring system according to claim 7, wherein the EIT device comprises:
a thorax electrode element provided with a plurality of electrodes for current injection and voltage detection, and attached along a chest circumference of a subject to be examined;

an impedance data obtainer configured to obtain impedance data about the thorax of the subject based on the voltage measured through the plurality of electrodes;

an algorithm function element configured to separate the lung ventilation impedance data, the lung perfusion impedance data and the bloodstream impedance data by applying a signal separating algorithm to the obtained impedance data; and an EIT controller configured to selectively supply electric currents to at least one pair of electrodes selected among the plurality of electrodes, measure voltage through unselected electrodes, and control the lung ventilation impedance data, the lung perfusion impedance data and the bloodstream impedance data to be transmitted.

10. The image monitoring system according to claim 9, wherein the algorithm function element applies an independent component analyses (ICA) algorithm, i.e. the signal separating algorithm to the obtained impedance data to separate the lung ventilation impedance data, the lung perfusion impedance data and the bloodstream impedance data, which are different from one another, and applies a signal magnitude restoration algorithm to each piece of the separated impedance data to be restored to have a magnitude of an original signal.

11. The image monitoring system according to claim 9, wherein the EIT controller comprises:

a current injection module configured to inject electric currents having a plurality of frequency ranges to at least one pair of electrodes selected among the plurality of electrodes attached to the thorax of the subject;

a voltage measuring module configured to measure voltage induced by the injected currents, through the unselected electrodes among the plurality of electrodes; and an EIT control module configured to control selection of at least one pair of electrodes among the plurality of electrodes, and control selection of the unselected electrodes.

12. The image monitoring system according to claim 11, wherein the current injection module selects the selected pair of electrodes and a frequency, generates and converts a voltage signal into a current corresponding to the selected frequency, and injects the converted current to the thorax of the subject through the selected pair of electrodes.

13. An image monitoring method of monitoring a state of a subject in real time through an image monitoring apparatus, the image monitoring method comprising:

receiving at least one of lung ventilation impedance data, lung perfusion impedance data and bloodstream impedance data, which are separated from voltage measured at a thorax of a subject by an electrical impedance tomography (EIT) device;

generating at least one of a lung ventilation impedance image, a lung perfusion impedance image and a bloodstream impedance image based on the lung ventilation impedance data, the lung perfusion impedance data and the bloodstream impedance data; and controlling at least one of the lung ventilation impedance image, the lung perfusion impedance image, and the bloodstream impedance image to be displayed according to screen modes and measurement parts, wherein the measured voltage is separated into the lung ventilation impedance data, the lung perfusion impedance data, and the bloodstream impedance data prior to generating the lung ventilation impedance image, the lung perfusion impedance image, and the bloodstream impedance image.

* * * * *